United States Patent
Do et al.

(10) Patent No.: US 10,499,845 B2
(45) Date of Patent: Dec. 10, 2019

(54) METHOD AND DEVICE FOR ANALYSING AN IMAGE

(71) Applicants: SINGAPORE UNIVERSITY OF TECHNOLOGY AND DESIGN, Singapore (SG); NATIONAL SKIN CENTRE (SINGAPORE) PTE LTD, Singapore (SG)

(72) Inventors: Thanh-Toan Do, Singapore (SG); Yiren Zhou, Singapore (SG); Victor Pomponiu, Singapore (SG); Ngai-Man Cheung, Singapore (SG); Dawn Chin Ing Koh, Singapore (SG); Tan Suat Hoon, Singapore (SG)

(73) Assignees: SINGAPORE UNIVERSITY OF TECHNOLOGY AND DESIGN, Singapore (SG); NATIONAL SKIN CENTRE (SINGAPORE) PTE LTD, Singapore (SG)

( * ) Notice: Subject to any disclaimer, the term of this patent is extended or adjusted under 35 U.S.C. 154(b) by 70 days.

(21) Appl. No.: 15/507,107

(22) PCT Filed: Aug. 25, 2015

(86) PCT No.: PCT/SG2015/050278
§ 371 (c)(1),
(2) Date: Feb. 27, 2017

(87) PCT Pub. No.: WO2016/032398
PCT Pub. Date: Mar. 3, 2016

(65) Prior Publication Data
US 2017/0231550 A1   Aug. 17, 2017

(30) Foreign Application Priority Data

Aug. 25, 2014   (SG) ........................ 10201405182W

(51) Int. Cl.
*G06K 9/32*       (2006.01)
*A61B 5/00*       (2006.01)
(Continued)

(52) U.S. Cl.
CPC ............ *A61B 5/444* (2013.01); *A61B 5/0077* (2013.01); *A61B 5/1032* (2013.01);
(Continued)

(58) Field of Classification Search
CPC .................. A61B 5/1032; A61B 5/444; G06T 2207/30088
See application file for complete search history.

(56) References Cited

U.S. PATENT DOCUMENTS

| 5,016,173 A * | 5/1991 | Kenet ............. A61B 5/0059 382/128 |
| 2002/0039434 A1* | 4/2002 | Levin .................. G16H 10/40 382/128 |

(Continued)

FOREIGN PATENT DOCUMENTS

| WO | 98/37811 A1 | 9/1998 |
| WO | 2008/064120 A2 | 5/2008 |

(Continued)

OTHER PUBLICATIONS

B. Basavaprasad et al. "A Survey on Traditional and Graph Theoretical Techniques for Image Segmentation", 2014, International Journal of Computer Applications, Recent Advances in Information Technology, p. 38-46 (Year: 2014).*

(Continued)

*Primary Examiner* — Gandhi Thirugnanam
(74) *Attorney, Agent, or Firm* — Osha Liang LLP

(57) ABSTRACT

A method for analyzing an image of a lesion on the skin of a subject including (a) identifying the lesion in the image by differentiating the lesion from the skin; (b) segmenting the
(Continued)

Flowchart of segmentation procedure image; and (c) selecting a feature of the image and comparing the selected feature to a library of predetermined parameters of the feature. The feature of the lesion belongs to any one selected from the group: color, border, asymmetry and texture of the image.

20 Claims, 13 Drawing Sheets

(51) Int. Cl.

| | | |
|---|---|---|
| *A61B 5/103* | (2006.01) | |
| *G06T 7/00* | (2017.01) | |
| *G06T 7/11* | (2017.01) | |
| *G06T 7/90* | (2017.01) | |
| *G06K 9/38* | (2006.01) | |
| *G06K 9/46* | (2006.01) | |
| *G06K 9/48* | (2006.01) | |

(52) U.S. Cl.
CPC ............ *A61B 5/6898* (2013.01); *A61B 5/726* (2013.01); *A61B 5/7264* (2013.01); *G06K 9/3233* (2013.01); *G06K 9/38* (2013.01); *G06K 9/4652* (2013.01); *G06K 9/48* (2013.01); *G06T 7/0012* (2013.01); *G06T 7/11* (2017.01); *G06T 7/90* (2017.01); *G06K 2209/053* (2013.01); *G06T 2207/10024* (2013.01); *G06T 2207/20016* (2013.01); *G06T 2207/20021* (2013.01); *G06T 2207/30088* (2013.01); *G06T 2207/30096* (2013.01)

(56) References Cited

U.S. PATENT DOCUMENTS

| | | | | |
|---|---|---|---|---|
| 2005/0036668 | A1* | 2/2005 | McLennan | G06K 9/4652 382/128 |
| 2008/0214907 | A1* | 9/2008 | Gutkowicz-Krusin | A61B 5/0059 600/306 |
| 2008/0226151 | A1* | 9/2008 | Zouridakis | A61B 5/0059 382/133 |
| 2008/0253627 | A1* | 10/2008 | Boyden | A61B 6/145 382/128 |
| 2009/0245603 | A1* | 10/2009 | Koruga | A45D 44/00 382/128 |
| 2010/0302358 | A1* | 12/2010 | Chen | A61B 5/0059 348/77 |
| 2011/0040192 | A1* | 2/2011 | Brenner | A61B 5/0059 600/476 |
| 2012/0008838 | A1* | 1/2012 | Guyon | G06N 99/005 382/128 |
| 2013/0245435 | A1* | 9/2013 | Schnaars | A61B 6/03 600/425 |
| 2014/0350395 | A1* | 11/2014 | Shachaf | G06T 7/0012 29/401.1 |
| 2016/0110632 | A1* | 4/2016 | Kiraly | G06K 9/66 382/128 |
| 2017/0007211 | A1* | 1/2017 | Ichikawa | A61B 8/14 |
| 2017/0231550 | A1* | 8/2017 | Do | G06T 7/11 382/128 |

FOREIGN PATENT DOCUMENTS

| | | |
|---|---|---|
| WO | 2008/109421 A1 | 9/2008 |
| WO | 2011/087807 A2 | 7/2011 |
| WO | 2013/149038 A1 | 10/2013 |

OTHER PUBLICATIONS

M. Messadi et al. "Extraction of specific parameters for skin tumour classification", Journal of Medical Engineering & Technology, vol. 33, No. 4, May 2009, 288-295 (Year: 2009).*
Wadhawan, T. et al.; "SkinScan©: A Portable Libary for Melanoma Detection on Handheld Devices"; Proc IEEE Int Sump Biomed Imaging, vol. 2011, Mar. 30, 2011, pp. 133-136 (12 pages).
Wadhawan, T. et al.; "Implementation of the 7-Point Checklist for Melanoma Detection on Smart Handheld Devices"; Conf Proc IEEE Eng Med Biol Soc., vol. 2011, Aug. 2011, pp. 3180-3183 (13 pages).
Do, T. et al.; "Early melanoma diagnosis with mobile imaging"; Conf Proc IEEE Eng Med Biol Soc. 2014, Aug. 30, 2014, pp. 6752-6757 (7 pages).
Toan, D. et al.; "Designing a mobile imaging system for early melanoma detection"; Mar. 24, 2015 (14 pages).
Mohamed, H. R.; "Minimum Spanning Tree Algorithm and Connected Components for Skin Cancer Image Object Detection"; Journal of College of Education for Pure Sciences, vol. 4, No. 1, Dec. 31, 2014, pp. 242-253 (12 pages).
Celebi, M. E. et al.; "A methodological approach to the classification of dermoscopy images"; Comput Med Imaging Graph, Sep. 2007, pp. 1-25 (25 pages).
Cho, T. S. et al.; "A reliable skin mole localization scheme"; In Computer Vision, 2007. /CCV 2007. IEEE 11th International Conference on, pp. 1-8 (8 pages).
Ganster, H. et al.; "Automated Melanoma Recognition"; IEEE Transactions on Medical Imaging, Mar. 2001, vol. 20, No. 3, pp. 233-239 (8 pages).
Lee, H. Y. et al.; "Melanoma: Differences between Asian and Caucasian Patients"; Ann Acad Med Singapore, vol. 41, No. 1, Jan. 2012, pp. 17-20 (4 pages).
American Academy of Dermatology; "What to look for: The abcde of melanoma"; <http://www.aad.org/spot-skin-cancer/understanding-skin-cancer/>how-do-i-check-my- skin/what-to-look-for/, Accessed Mar. 6, 2013 (3 pages).
Peng, H. et al.; "mRMR FAQ."; http://penglab.janelia.org/prni/rnRMRiFAO. mrrnr.htm/, Accessed Mar. 6, 2013 (11 pages).
La Torre, E. et al.; "Kernel Methods for Melanoma Recognition"; MIE, pp. 983-988 (6 pages).
Xu, L. et al.; "Segmentation of skin cancer images"; Image and Vision Computing, 17, 1999, pp. 65-74 (10 pages).
Supplementary International Search Report issued in PCT/SG2015/050278 dated Aug. 16, 2016 (6 pages).
Written Opinion of the International Searching Authority issued in PCT/SG2015/050278 dated Dec. 15, 2015 (4 pages).
International Preliminary Report on Patentability from PCT/SG2015/050278, dated Feb. 28, 2017 (5 pages).

* cited by examiner

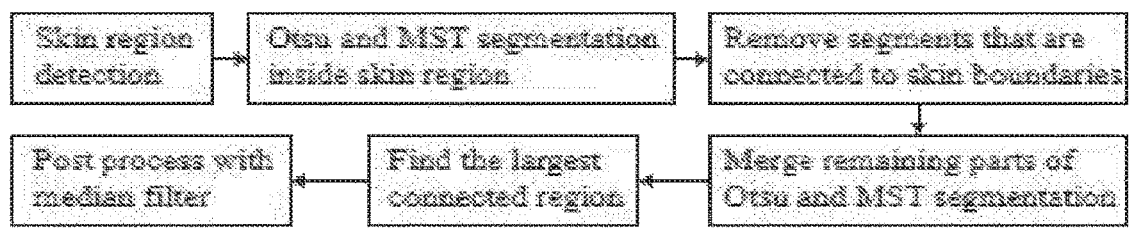
Figure 1(a) Flowchart of segmentation procedure
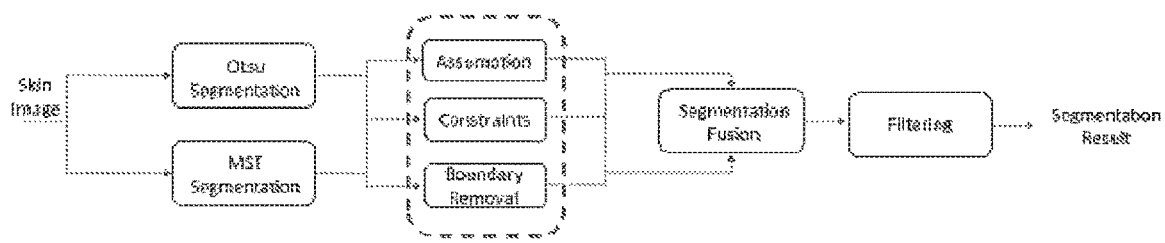
Figure 1(b)

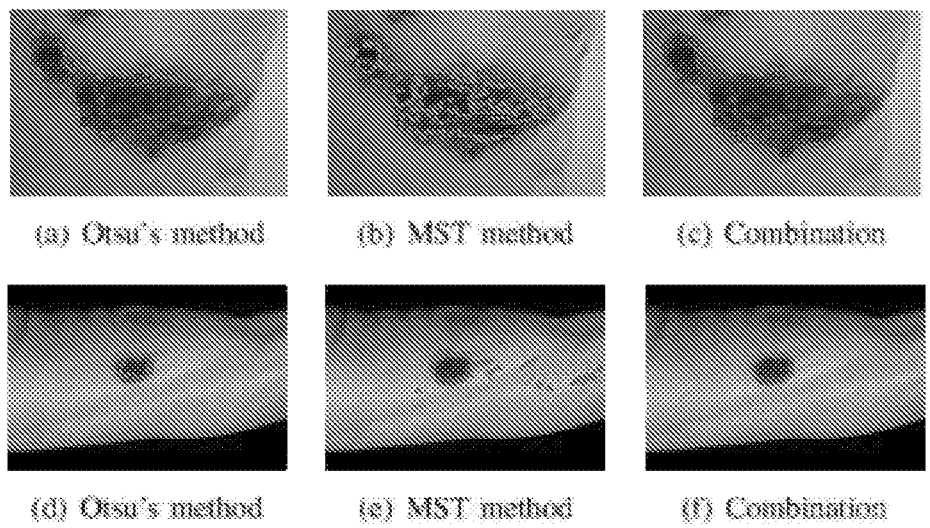
Fig. 2. Results of our proposed segmentation scheme. Images (a-c) are segmentation results by using Otsu's method, MST method, and combination of two methods for the first example. Images (d-f) are the segmentation results for the second example.
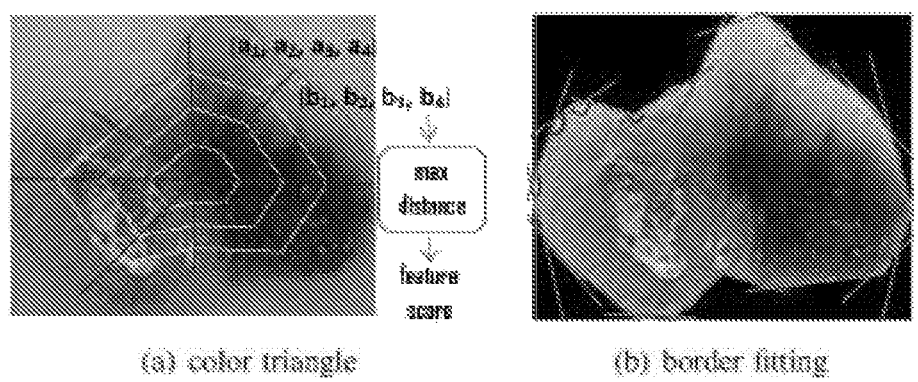
Fig. 3. Our proposed feature to quantify color variation (a) and border irregularity (b) of a skin lesion

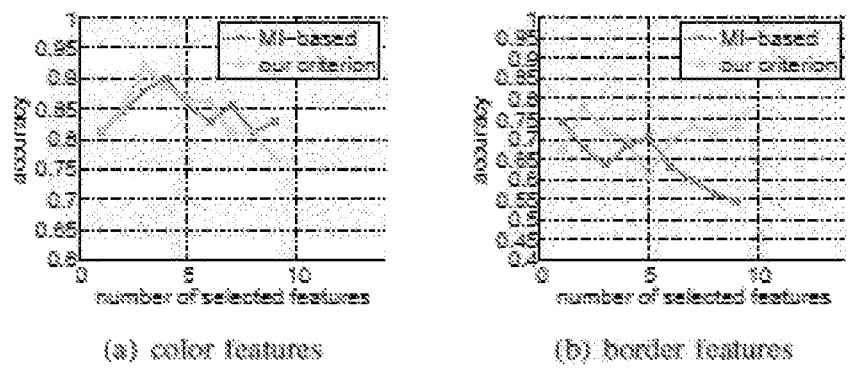
(a) color features  (b) border features
Fig. 4. classification accuracy for different number selected features when proposed criterion and MI-based criterion are used to select color features (a) and border features (b)
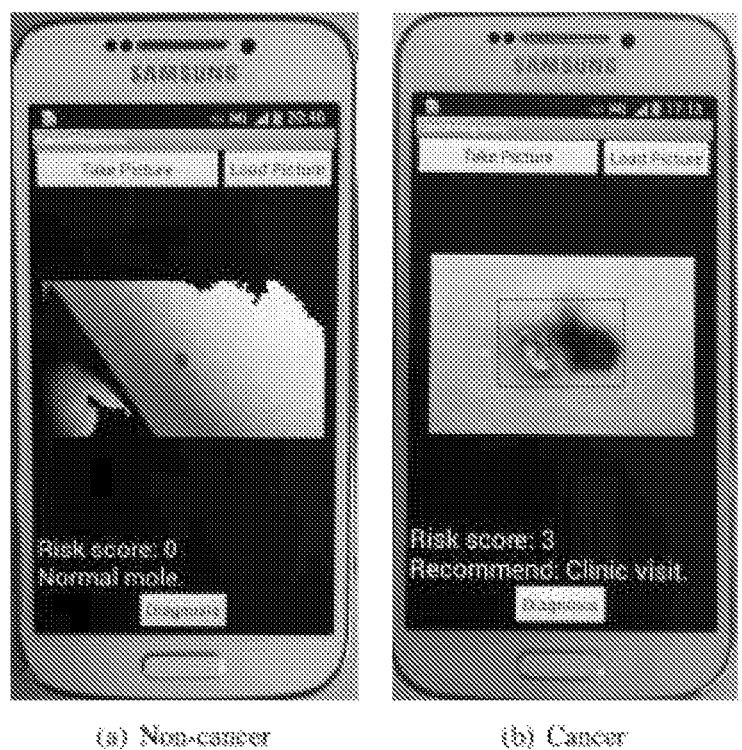
(a) Non-cancer  (b) Cancer
Fig. 5. Screenshot of application. (a) is a non-cancer sample. (b) is a cancer sample.

METHOD AND DEVICE FOR ANALYSING AN IMAGE

This application claims the benefit of Singapore patent application number 10201405182 W filed 25 Aug. 2014, the entire contents of which is herein incorporated by reference.

This invention relates to a novel mobile imaging system. In particular, it relates to a smartphone imaging system that may be suitable for the early detection of melanoma.

Malignant melanoma (MM) is a type of skin cancer arising from the pigment cells of the epidermis. There are three main types of skin cancers: MM, basal cell carcinoma (BCC) and squamous cell carcinomas (SCC). Nevertheless, MM is considered most hazardous, and the most aggressive form of skin cancer, with an estimated mortality rate of 14% worldwide. It is responsible for the majority of skin cancer related deaths. According to the annual report "Cancer facts and figures", the American Cancer Society projected 73,870 new case s of melanoma in United States in 2015, with almost 9,940 estimated deaths. Furthermore, the global cancer statistics also emphasis on the rising trend of the incidence and mortality rates of MM. Fortunately, melanoma may be treated successfully yet the curability depends on its early detection and removal when the tumor is still relative small and thin. However, in some countries, there is a trend towards more advanced disease staging at presentation, due to lack of patients' awareness and delayed or missed diagnosis by primary care physicians [12]. There is a pressing need for an accessible and accurate pre-screening solution to improve the general awareness.

The process of diagnosing melanoma is complex and inherently subjective, relying mainly on the use of naked eye examination. Therefore, the diagnosis accuracy highly depends on the experience of dermatologists, which is considered to be around 85%. In order to boost the detectability of MM, researchers have suggested the use of other visual inspection techniques such as dermoscopy, spectroscopy and analytical reasoning techniques like the ABCDE rule (which stands for Asymmetry of lesion, Border irregularity, Color variation, Diameter and Evolving), the 7-point checklist, and the Menzies method.

Nowadays our industry faces the junction of two rapidly developing markets: healthcare and mobile technology. This increased availability of mobile devices equipped with multicore CPUs graphic processing units, rich multimedia touch displays and high resolution image sensors allows people to become more proactive and involved in their own healthcare process.

Increasingly, smartphones are equipped with multi-core CPUs and high resolution image sensors. All this creates the opportunity to use a smartphone to analyze a captured image for disease diagnosis and self-screening.

Several automatic melanoma diagnosis systems have been proposed in the literature [14], [10], [2], [20]. However, they focus on dermoscopic images (including [22], which uses mobile phones for dermoscopic image analysis). Dermoscopic images are taken with the aid of liquid medium or non-polarised light source and magnifiers, under well-controlled clinical conditions. Dermoscopic images include features below the skin surface, which cannot be captured with normal cameras equipped in smartphones. There have been a few isolated work that investigated images captured from smartphone. In [19], a mobile-system working for images taken from mobile camera is presented. However, to detect lesion, they used a very basic thresholding method. To describe a lesion, only simple color features (mean/variance of some color channels, the difference of color through vertical axis) and border features (convexity, compactness) were extracted, and these features are subjected to a simple kNN classifier. It is unclear about the accuracy of their proposed system. [4] also focuses on images taken from mobile camera. The lesion detection and feature extraction are performed on mobile devices while the classification can be performed on the mobile device or in a cloud environment. However, in that work, the emphasis is on system integration, and the authors did not clearly mention what algorithms/features were used for diagnosis.

Generally, an automatic melanoma detection system can be divided into three main stages of segmentation, feature extraction, and classification. Some algorithms have been investigated for dermoscopic images taken under well-controlled conditions, but there is little attention on smartphone captured images taken under loosely-controlled lighting and focal conditions.

The segmentation stage aims to determine lesion region from captured images. There are several common methods to perform lesion segmentation [25], [2]: histogram thresholding, clustering, edge-based, region-based, and active contours. Among these methods, histogram thresholding and region-based are most often used. Histogram thresholding methods use image histogram to determine one or more intensity values for separating pixels into groups. The most popular thresholding method for lesion segmentation is Otsu's method [16]. Region-based methods form different regions by using region merge or region split methods.

The feature extraction stage aims to extract features that describe the lesion. There are many methods proposed such as pattern analysis, Menzies method, ELM 7-point checklist, etc. [24]. However, again, most of these methods are usually applied to images taken from a dermatoscope. For melanoma, the most important warning sign is a new or changing skin growth. It could be a new growth or a change in the color, size or shape of a spot on the skin. To help people to carry out self-examinations their skin, American Academy of Dermatology promoted a simple method called "ABCDE" [15] corresponding to Asymmetry of lesion, Border irregularity, Color variation, Diameter and Evolving. There are many methods used in the literature to capture color variation, border irregularity, asymmetry because computer-aided diagnosis systems usually perform diagnosis based on a single image. Evolving features are not used generally. The reviews can be found in [14], [10], [2].

Although there are many features used in previous work to describe color variation and border irregularity, most of these features are general features such as mean, variance of different color channels; compactness, convexity, solidity of shape. They are not specifically designed to capture color and border information of lesion.

As such, there is a need for an improved mobile system and method for the early diagnosis of melanoma that is quick, accurate, and less taxing on the power and memory capacity of the mobile device, robust to noise and distortion that arises in uncontrolled image-capturing environments, and tuned for visible light images captured using mobile systems.

In accordance with a first aspect of the invention, there is provided a method for analysing an image of a lesion on the skin of a subject, the method comprising: (a) identifying the lesion in the image by differentiating the lesion from the skin; (b) segmenting the image; and (c) selecting a feature of the image and comparing the selected feature to a library of predetermined parameters of the feature, wherein the feature of the lesion belongs to any one selected from the group: colour, border, asymmetry and texture of the image.

In the present invention, advantageously, we design the modules of what could be known as a mobile heath (mHealth) system for the automatic melanoma detection using user-captured color images. The proposed system has two major components. The first component is a fast and lightweight segmentation algorithm for skin detection and accurate lesion localization. The second component, used to automatically assess the malignancy of the skin lesion image, incorporates new computational features to improve detection accuracy, new feature selection tools to enable on-device processing (no access to remote server/database being required) and a combined classification model.

An iterative design approach was used to assess and improve the performance and clinical utility of the new mobile application. The design was based upon a commercially available Smartphone. We extensively study the system in pre-clinical settings, based on large number of pre-selected digital images of MMs and benign nevi.

Although melanoma diagnosis systems have been proposed here for different image modalities, we restrict our attention to mobile solutions or to those that can be adapted to the connected mHealth ecosystem.

Preferably, the image is processed prior to identifying the lesion in the image. Such a processing comprises down-sampling the image.

Preferably, segmenting the image further comprising a first segmenting and a second segmenting, the first segmenting determines an uncertain region on the image and the second segmenting refines the uncertain region to obtain segment boundary details. The first segmenting process may be a coarse segmenting to determine any uncertain regions of the image, and the second segmenting process may be a fine segmenting carried out on the coarse segmentation to refine the uncertain regions to obtain segment boundary details. Uncertain regions may be an image region in the original resolution image where pixel labels are uncertain after the first coarse segmentation. In an embodiment, the uncertain region is about +/−2 pixels around the coarse segmentation region boundary. Preferably, the second segmenting process to refine the uncertain region is carried out using a MST-based algorithm.

Preferably, each group is further divided into sub-groups and the feature selected is based on whether that feature is far from other features belonging to other sub-groups, but near to other features within the same sub-group.

Preferably, the lesion in the image is identified by comparing the colour of the skin to a library of predetermined colours.

Preferably, segmenting the lesion further comprising removing segments of the lesion that are connected to the skin boundary.

In addition, or alternatively, segmenting the image is a result of two segmentations: (a) a minimal intra-class-variance thresholding algorithm to locate smoothly-changing borders; and (b) a minimal-spanning-tree based algorithm to locate abruptly-changing borders.

Preferably, segmenting is carried out by a region-based method, i.e. group together pixels being neighbours and having similar values and split groups of pixels having dissimilar values.

Preferably, method further comprises quantifying the colour variation and border irregularity of the image of the lesion. Colour variation may be quantified by (a) dividing image into N-partitions, each partitions further divided into M-subparts; (b) calculating an average pixel value for each subpart and assigning a vector to the subpart; and (c) determining the maximum distance between the vectors, wherein the value of N is any value 4, 8, 12 or 16; and the value of M is any value 2, 4 or 8. Irregularity of the border is determined by (a) providing lines along the border; (b) determining the angles between two adjacent lines; and (c) determining the average and variance of the angles, wherein the number of lines chosen is any number 8, 12, 16, 20, 24 or 28.

Preferably, the lesion is present in a tissue having a dermal-epidermal junction and an epidermal layer. Preferably, the present method may differentiate between histological subtypes of cutaneous melanoma. In an embodiment, the lesion is an acral lentiginous melanoma.

Preferably, the method further comprising acquiring the image on a computing device and the analysis carried out on the same computing device.

Preferably, the image of the object is taken using a smartphone mobile device. Such images are unlike previous work focused on ELM images (epiluminescence microscopic or dermoscopic images), XLM (cross-polarization ELM) or TLM (side-transillumination ELM) that are captured in clinical environments with specialized equipment and skills. Images taken using a smartphone mobile device are simply visual images of the object "as is", i.e. topical appearance of the object. Using such images to evaluate the risk or likelihood of a disease or condition simply on the topical appearance of the object poses its own set of challenges which this invention seeks to overcome. These will be described in detail below.

Preferably, the method of the present invention may be used to evaluating the risk or likelihood of, or diagnose, a disease or condition. The disease is melanoma.

In accordance with a second aspect of the invention, there is provided device for analysing an image of an object and evaluating the risk or likelihood of a disease or condition, the system comprising: (a) an image capturing device for capturing the image of an object; and (b) a processor for executing a set of instructions stored in the device for analysing the image, the set of instructions includes a library of algorithms stored in the device to carry out a method according to the first aspect of the invention.

Preferably, the object is a lesion on a patient's body and the disease is melanoma.

Preferably, the device further comprising a graphical user interface for indicating to a user the results of the analysis.

Depending on the mechanism used to evaluate the skin lesion, melanoma diagnosis schemes can be classified into the following classes: manual methods, which require the visual inspection of an experienced dermatologist and automated (computed-aided) schemes that perform the assessment without human intervention. A different class, called hybrid approaches, can be identified when dermatologists jointly combine the computer-based result, context knowledge (e.g., skin type, age, gender) and his experience during the final decision. In general, an automatic melanoma analysis system can be constructed in four main phases. The first phase is the image acquisition which can be performed though different devices such as dermatoscope, spectroscope, standard digital camera or camera phone. The images acquired by these devices exhibit peculiar features and different qualities, which can significantly change the outcome of the analysis process. The second phase involves the skin detection, by removing artifacts (e.g., ruler, watch, hair, scar), and mole border localization. The third phase computes a compact set of discriminative features, describing the mole region. Finally, the fourth phase aims to build a classification model for the MM lesions based on the extracted features.

It is worth pointing out that most of the existing approaches are mainly suitable for dermatoscopic or spectroscopic images and they do not provide a complete solution that integrates both the segmentation and classification steps. Dermoscopic images are acquired under controlled clinical conditions by employing a liquid medium (or a non-polarized light source) and magnifiers. This type of image includes features below the skin surface which cannot be captured with standard cameras. Therefore, these settings limit the generality and availability of dermatoscopic and spectroscopic systems since they do not consider the lesion localization and, in some cases, apply a complicated set-up. Recently, several mobile connected dermatoscopic devices have been developed, such as DermLite (3Gen Inc, CA, USA) and HandyScope (FotoFinder Systems, Bad Bimbach, Germany). Although the usability and mobility is greatly increased, the cost to acquire such an additional device is expensive and not accessible to everyone.

There is a plethora of computer-aided systems for segmentation and classification of dermatoscopic images. For instance, the common methods employed for lesion segmentation are based on histogram thresholding, adaptive thresholding, difference of Gaussian (DoG) filter, morphological thresholding, hybrid thresholding on optimal color channels, deformable models, wavelet transform, wavelet neural networks, iterative classification, clustering, edge and region merging, fuzzy sets, active contours, adaptive snake and random walker algorithm.

On the other hand, the features used to accurately classify MM from dermatoscopic images are devised in such a way that they can describe dermatologist-observed characteristics such as color variation, border irregularity, asymmetry, texture and shape. There are many methods used in the literature that capture these features. A model-based classification of the global dermatoscopic patterns have been proposed. The method employs a finite symmetric conditional Markov model in the color space and the resulted parameters are treated as features.

There are only few systems working on mobile platforms like Lubax (Lubax Inc, CA, USA),]. However, the these methods merely use the mobile device for capturing, storing and transmission of the skin lesion images to a remote server without performing any computation, such as image segmentation, feature computation and/or classification, locally on the mobile device. The images sent to the server for computer assessment could be acquired by the camera phone or by a mobile dermatoscope attached to the device. Another sub-category is Teledermatology and Teledermoscopy in which the remote assessment of the skin lesion images relies on the examination of a dermatologist. All these systems require a high bandwidth Internet connection and availability of dermatologists to diagnose the skin images.

A few isolated works perform the analysis of smartphone-captured (or dermatoscopic images) directly on the mobile device. For instance, a portable library for melanoma detection on handheld devices based on the well-known bag-of-features framework has been proposed. They showed that the most computational intensive and time consuming algorithms of the library, namely image segmentation and image classification, can achieve accuracy and speed of execution comparable to a desktop computer. These findings demonstrated that it is possible to run sophisticated biomedical imaging applications on smart phones and other handheld devices.

In accordance with a third aspect of the invention, there is provided a computer-readable medium including executable instructions to carry out a method according to the first aspect of the invention. In particular, an embodiment of the present invention relates to a computer storage product with a computer-readable medium having computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits ("ASICs"), programmable logic devices ("PLDs") and ROM and RAM devices. Examples of computer code include machine code, such as produced by a compiler, and files containing higher-level code that are executed by a computer using an interpreter. For example, an embodiment of the invention may be implemented using Java, C++, or other object-oriented programming language and development tools. Another embodiment of the invention may be implemented in hardwired circuitry in place of, or in combination with, machine-executable software instructions.

The present invention is designed for the early detection of skin cancer using mobile imaging and on-device processing. In particular, smartphone-captured skin mole images may be used together with a detection computation that resides on the smartphone. Smartphone-captured images taken under loosely-controlled conditions introduce new challenges for skin cancer detection, while on-device processing is subject to strict computation and memory constraints. To address these challenges and to achieve high detection accuracy, we propose a system design that includes the following novel elements:

Automatic feature selection: under the well-known Normalize Mutual Information Feature Selection (NMIFS) framework, we propose a mechanism to include the coordinate of the variable values to improve the feature selection results.

Skin mole localization using fast skin detection and fusion of two fast segmentation algorithms to localize the mole region: a minimal intra-class-variance thresholding algorithm to locate smoothly-changing mole borders and a minimal-spanning-tree based algorithm to locate abruptly-changing borders. This design leads to a localization scheme that is accurate and has small computation requirement.

New features to mathematically quantify the color variation and border irregularity of the skin mole; these features are specific for skin cancer detection and are suitable for mobile imaging and on-device processing. In particular, in an embodiment of the present invention, the invention detects the malignancy of a skin mole by measuring its concentric partitions' color uniformity, and the algorithms used by the present system and method quantify this. The present invention also uses a new border irregularity descriptor that is robust to image noise suitable for our image modality and capturing environment.

New feature selection mechanism that takes into account the coordinate of the feature values to identify more discriminative features A classifier array and a classification result fusion procedure to compute the detection results. The present invention uses an array of classifiers and results fusion that is more appropriate for this invention.

Previous systems and methods are based on epiluminescence microscopy (ELM) imaging used in the clinical environments. ELM images are taken with the aid of liquid medium or non-polarised light source and magnifiers, rendering the surface translucent and making subsurface structures visible. Thus, subsurface structures can be used to aid diagnosis. However, ELM images can only be captured by specially-trained medical professionals. On the contrary, the present system employs mobile imaging that captures visible light image and can be used by the general public. The present method addresses the limitations arisen in mobile imaging. In particular, the present invention performs the detection using on-device processing. This is in contrast to some systems that perform processing at remote servers. Note that processing at remote servers has several issues: (i) Privacy is compromised; in particular, mole checking involves images of body parts; (ii) Resource planning and set-up of the server infrastructure is required; (iii) Network connectivity and transmission delay may affect the diagnosis. On-device processing solves these issues. The present system is designed to enable accurate on-device detection under strict computation and memory constraints.

Still more particular, the system and method of the present invention focuses on two new features which can efficiently describe the color variation and border irregularity of lesion.

As indicated earlier, there are many features can be extracted to describe color, border or texture of lesion. It likely has some noise features also redundancy between features which may reduce the classification rate. Hence, a feature selection that is done in offline mode to select only good features is necessary. Only selected features will be used to judge if a lesion is cancer/non-cancer. Furthermore, feature selection has an important role in mobile-based diagnosis system where there are strict computational and memory constraints. Advantageously, by using a small number of features, it will have some benefits such as reduce feature extraction time and storage requirements; reduce training and testing time; reduce the complexity of classifier, and increase in classification accuracy in some cases.

Feature selection algorithms can be divided into two categories according to their evaluation criteria: wrapper and filter [13]. Wrapper approach uses the performance of a predetermined classifier to evaluate the goodness of features. On the other hand, filter approach does not rely on any classifiers. The goodness of features is evaluated based on how much the relevance between them and class labels. In this work, we follow filter approach because it is very fast which allows us to compare different methods. Furthermore, it is more general than wrapper approach because it does not involve to any specific classifier.

In filter approach, the relevance is usually characterized in terms of mutual information. However, the drawback of mutual information is that it only uses the probability of variables while ignoring the coordinate of variables which can help the classification. To overcome this drawback of mutual information, we propose a new feature selection criterion taking into account the coordinate of variables when evaluating the goodness of features.

The final stage of automatic melanoma detection is to classify extracted features of lesions into either cancer or non-cancer. Many classification models can be used at this stage such as Support Vector Machine (SVM), nearest neighbor, discriminant analysis [14], [10], [2].

In order that the present invention may be fully understood and readily put into practical effect, there shall now be described by way of non-limitative examples only preferred embodiments of the present invention, the description being with reference to the accompanying illustrative figures.

In the Figures:

FIG. 1 is (a) a flowchart showing the segmentation procedure and (b) a block diagram of the coarse lesion localisation according to an embodiment of the present invention.

FIG. 2 shows the results of legion segmentation according to an embodiment of the present invention.

FIG. 3 shows the quantification of color variation and border irregularity as carried out by a method according to an embodiment of the present invention.

FIG. 4 shows the classification accuracy with different number of selected color features carried out by a classification method according to an embodiment of the present invention.

FIG. 5 shows an illustration of a screenshot of an application indicating results and diagnosis according to an embodiment of the invention.

Figure 8:
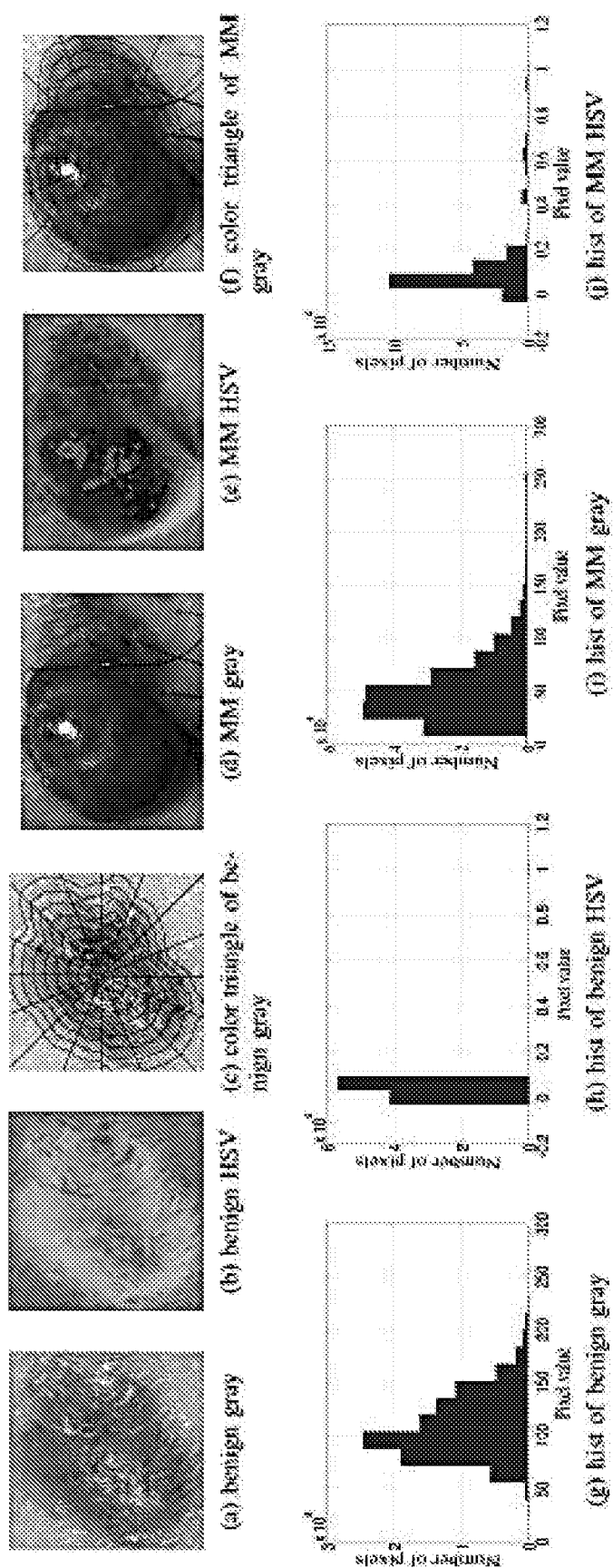

FIG. 8 show LCF for two skin images converted to the gray scale and HSV color space. FIGS. (8a) and (8b) are for the benign nevus and FIGS. (8d) and (8e) are for MM. The histograms shown in (8g)-(8j) count the number of pixels values in each bins. The black lines in (8c) and (8f) segment the lesion in partitions and subparts to calculate the CT feature.

Figure 9:
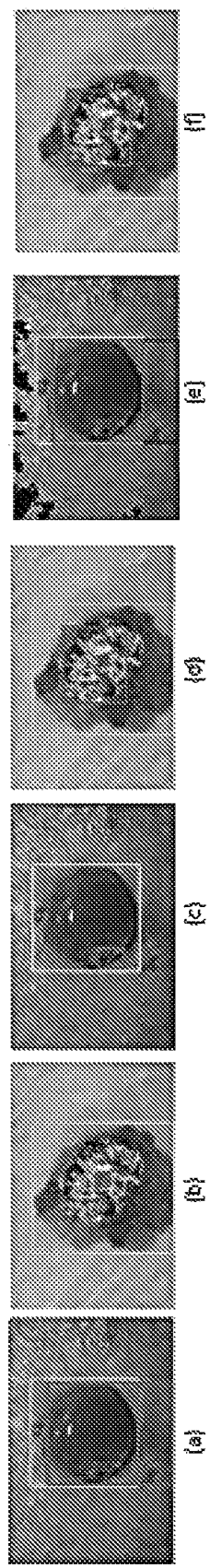

FIG. 9 show segmentation evaluation for the Otsu (a), (b), the MST (c), (d), and the proposed (e), (f) methods. The green rectangle represents the GT, the red rectangle denotes the SEG. The images under consideration are all MMs.

Figure 10:
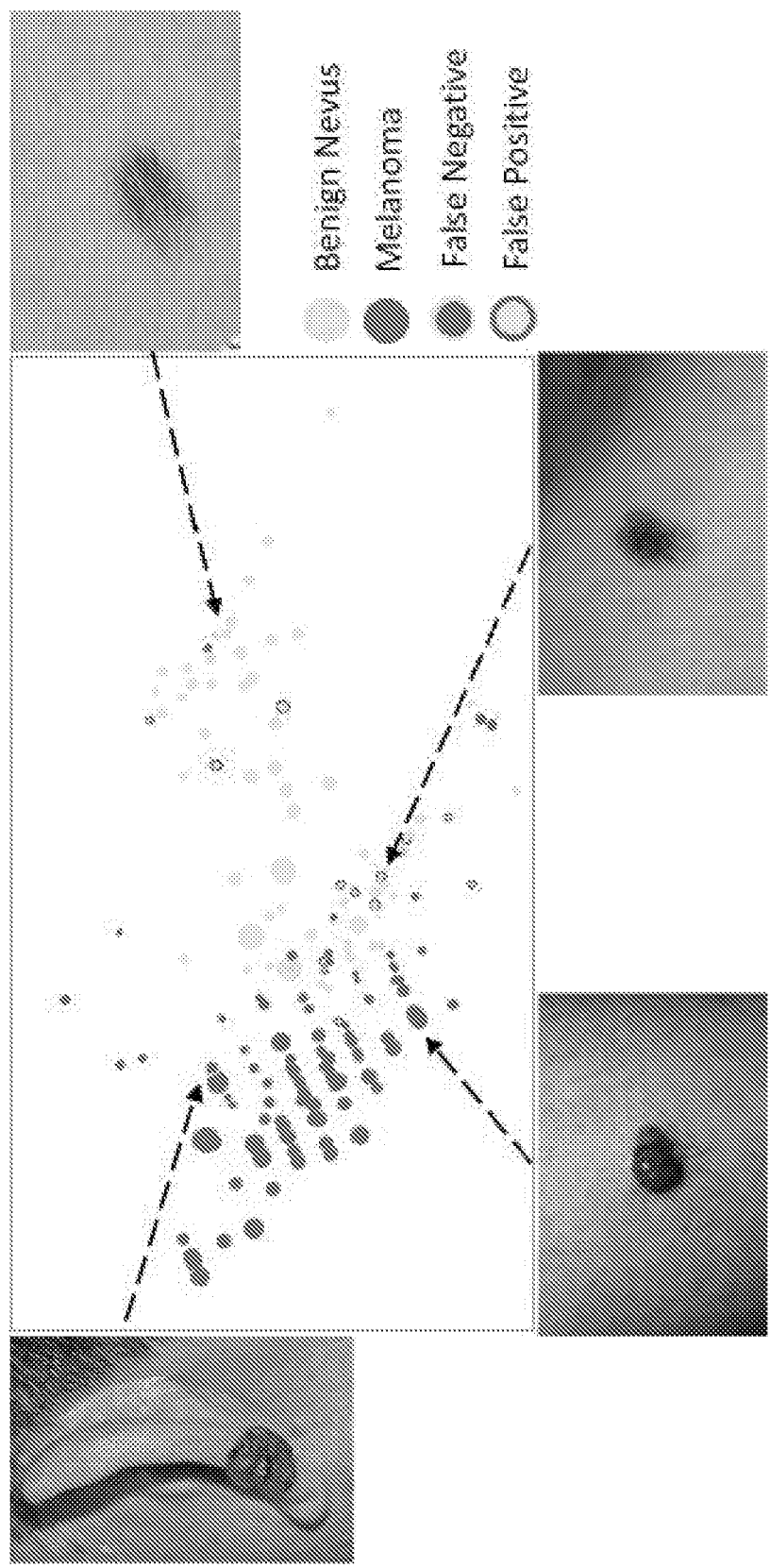

FIG. 10 show 2D visualization of SVM output of the LCF after dimension reduction for SET1 (117 benign nevi and 67 MMs).

Figure 11:
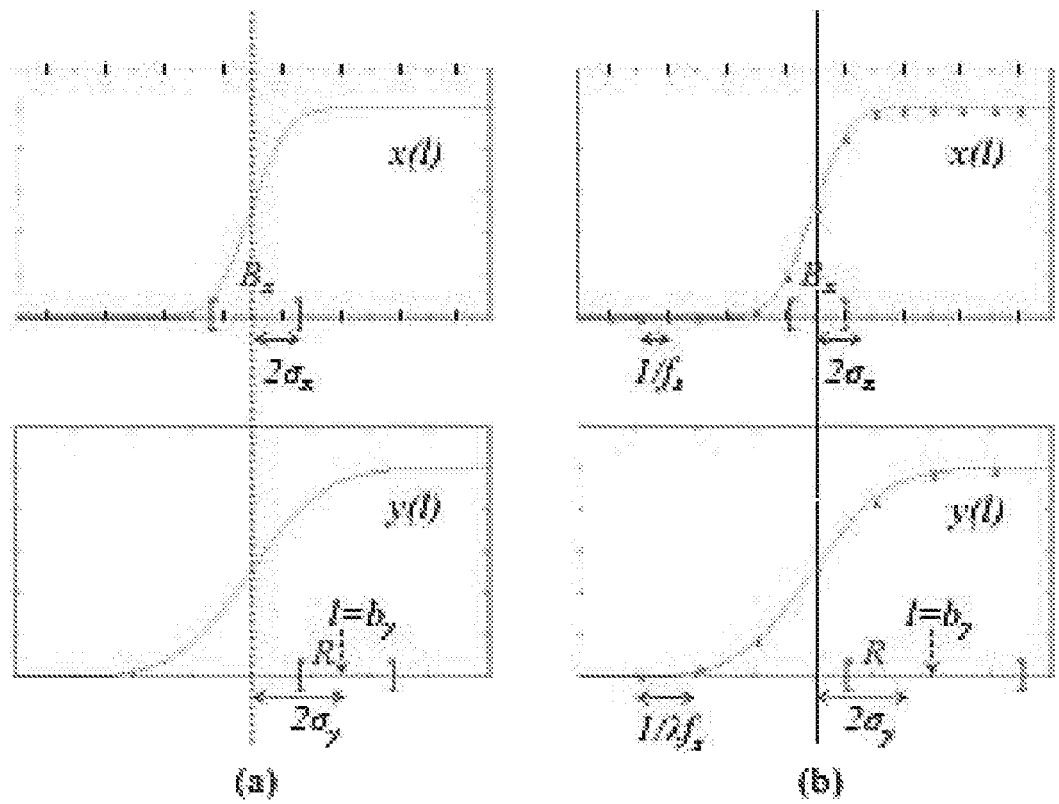

FIG. 11 show the analysis of the effect of downsampling on image segmentation. (a) Continuous domain analysis: A ramp boundarysignal x(l) (left-top) and its low-pass filtered counterpart y(l) (left-bottom). Refinement interval R is constructed so that it overlaps with Bx. (b) Discrete case: the discretized version of x(l) (right-top) and its downsampled counterpart (rightbottom). R and Bx are adjusted to take into account the effect of quantization. Tick marks on the horizontal axes depict sampling positions.

Figure 12:
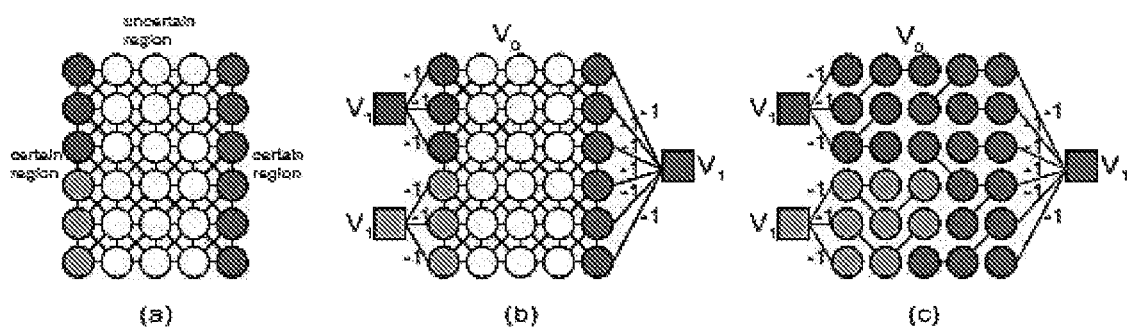

FIG. 12 show the graph creation according to an embodiment of the present invention. (a) The pixels are represented in circle nodes. The colored nodes represent boundary certain pixels, and uncolored nodes represent uncertain pixels. (b) Virtual nodes $V_1$ are introduced and connected with boundary certain nodes with (−1)-weight edges; $V_0$ includes both certain nodes and uncertain nodes. (c) The final segmentation result is produced by tree merging using the MST edges (blue edges).

Figure 13:
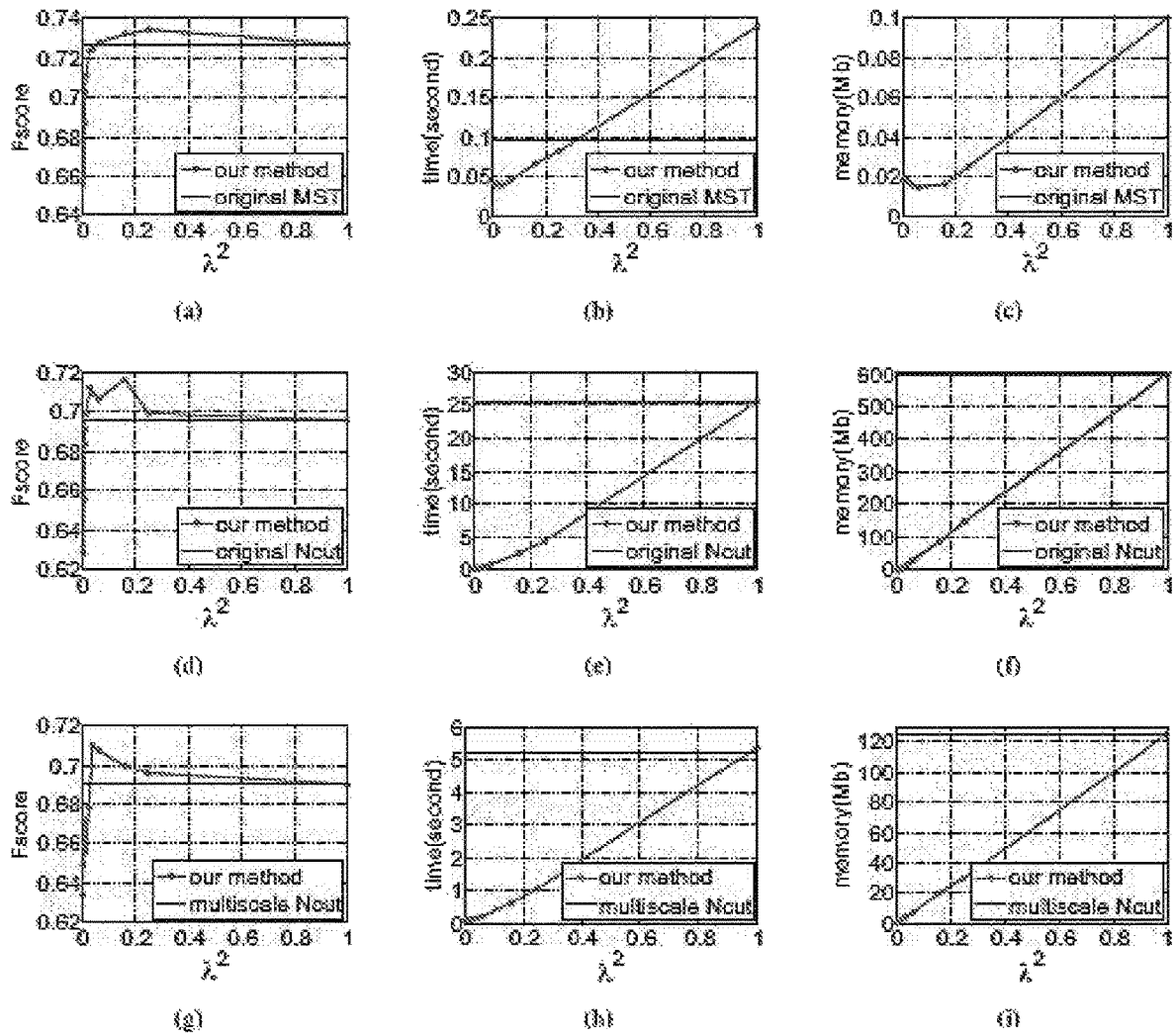

FIG. 13 show the accuracy, time, and memory usage on the single object dataset. (a-c) use MST to segment downsampled image, (d-f) use Ncut to segment downsampled image. (g-i) use multiscale Ncut to segment downsampled image. Results are the average of all images in database. The x-axis represents square of scale factor, i.e., the ratio of the number of pixels in the downsampled image to that of the original image. Memory usage is reported using Valgrind whenever it is feasible. However, for the memory comparison in (c) (original MST vs. MST in our framework), memory usage is too small to be reported accurately by Valgrind. Thus we analysis the program code to estimate the memory usage for this comparison.

Figure 14:
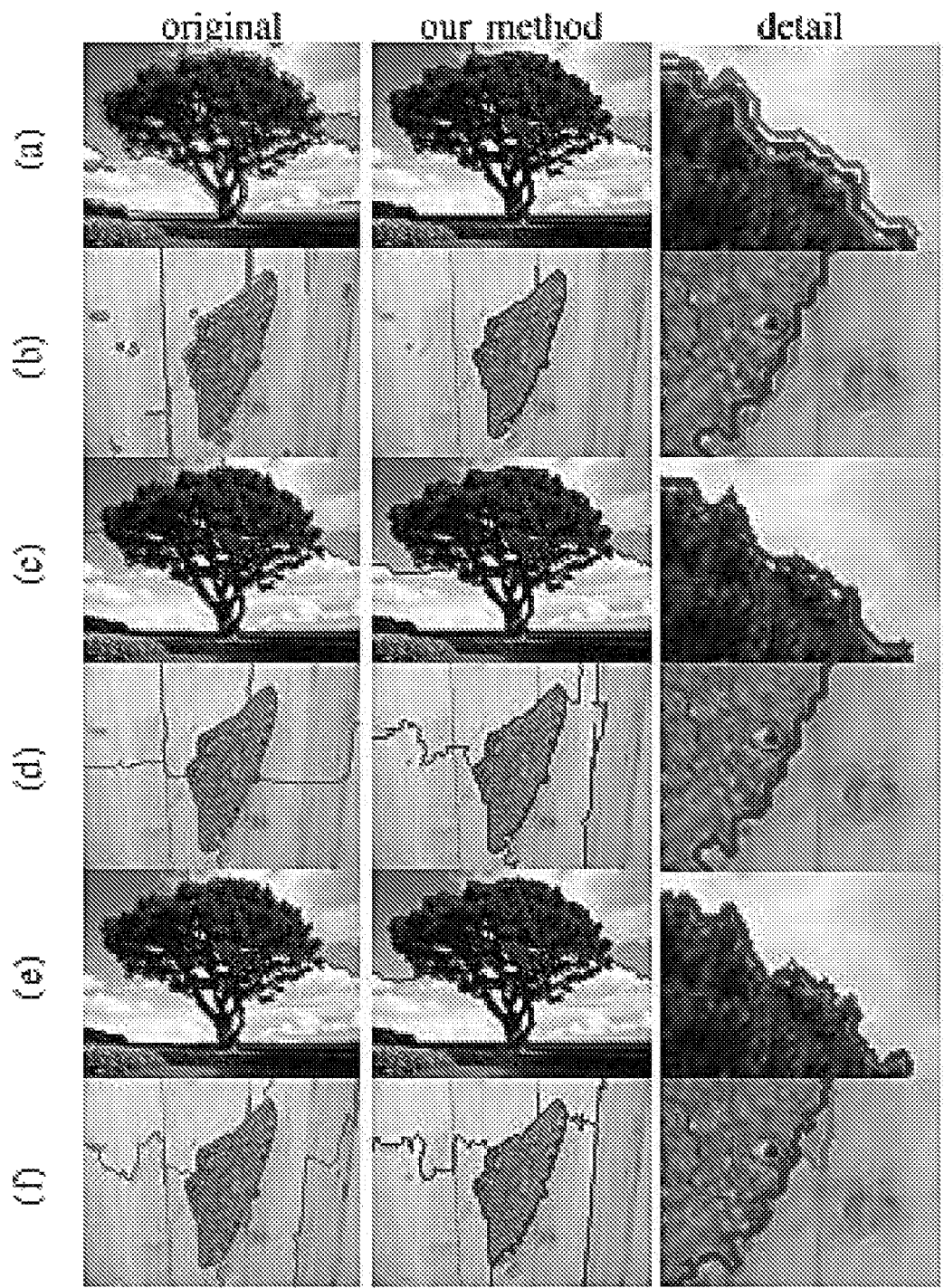

FIG. 14 show the segmentation results for sample images from single object dataset. Row (a-b) use MST algorithm, row (c-d) use Ncut algorithm, and row (e-f) use multiscale Ncut algorithm. In first column, the segmentation is applied on original image. In second column, first, the segmentation is applied on downsampled image. Then, our method is used for refinement. The third column shows the detail of two segmentations.

Figure 15:
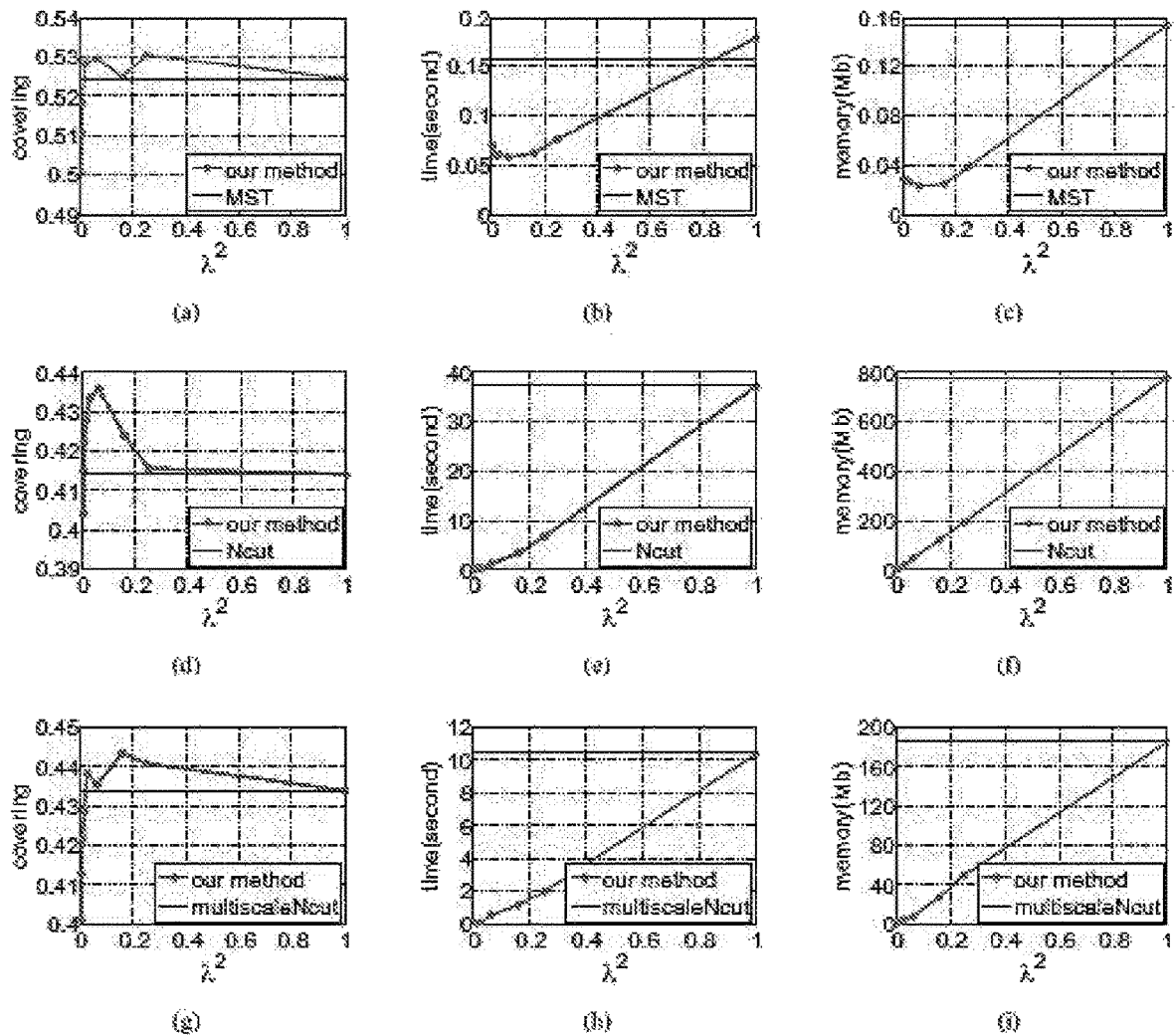

FIG. 15 show the accuracy, time, and memory performance on the BSDS500 dataset. (a-c) use MST to segment downsampled image, (d-f) use Ncut to segment downsampled image. (g-i) use multiscale Ncut to segment downsampled image. Here we use optimal dataset scale (ODS) of segmentation covering metric to represent accuracy of segmentation result. Results are computed on the average of all images in database. The x-axis represents square of scale factor, i.e., the ratio of the number of pixels in the downsampled image to that of the original image.

Figure 16:
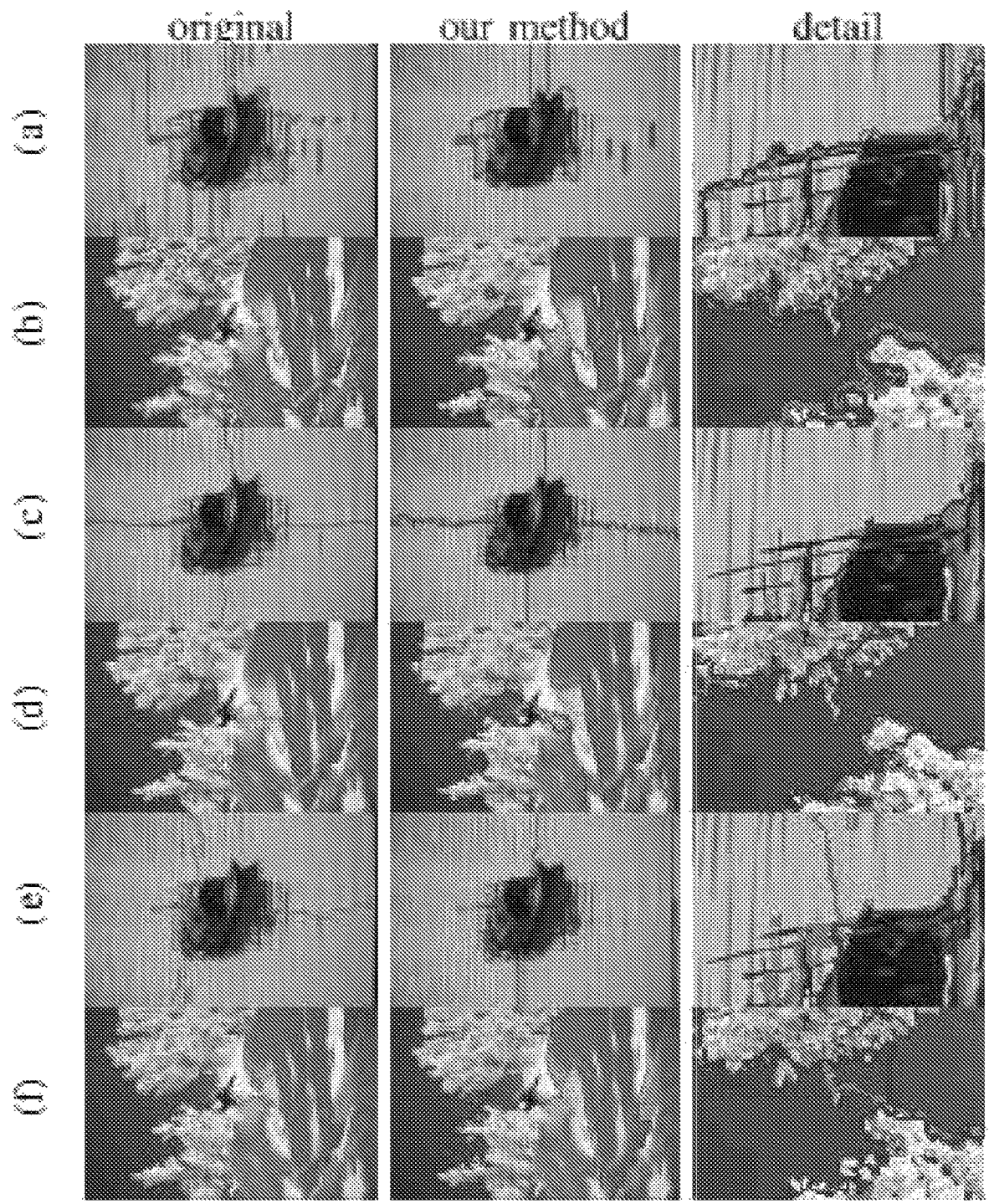

FIG. 16 show segmentation results for sample images from BSDS500 dataset. Row (a-b) use MST algorithm, row (c-d) use Ncut algorithm, and row (e-f) use multiscale Ncut algorithm. In first column, the segmentation is applied on original image. In second column, first, the segmentation is applied on downsampled image. Then, our method is used for refinement. The third column shows the detail of two segmentations.

Figure 17:
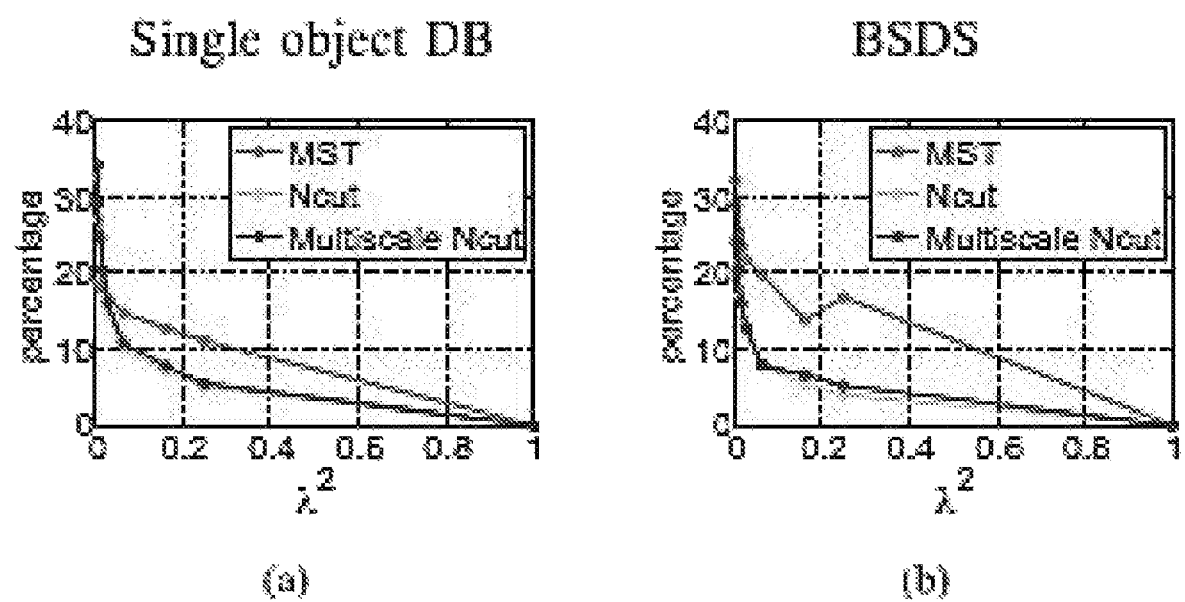

FIG. 17 show the percentage of pixels on uncertain area. The left figure (a) shows the percentage on single object dataset, and the right (b) on BSDS500 dataset.

All publications and patent applications herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Figure 6:
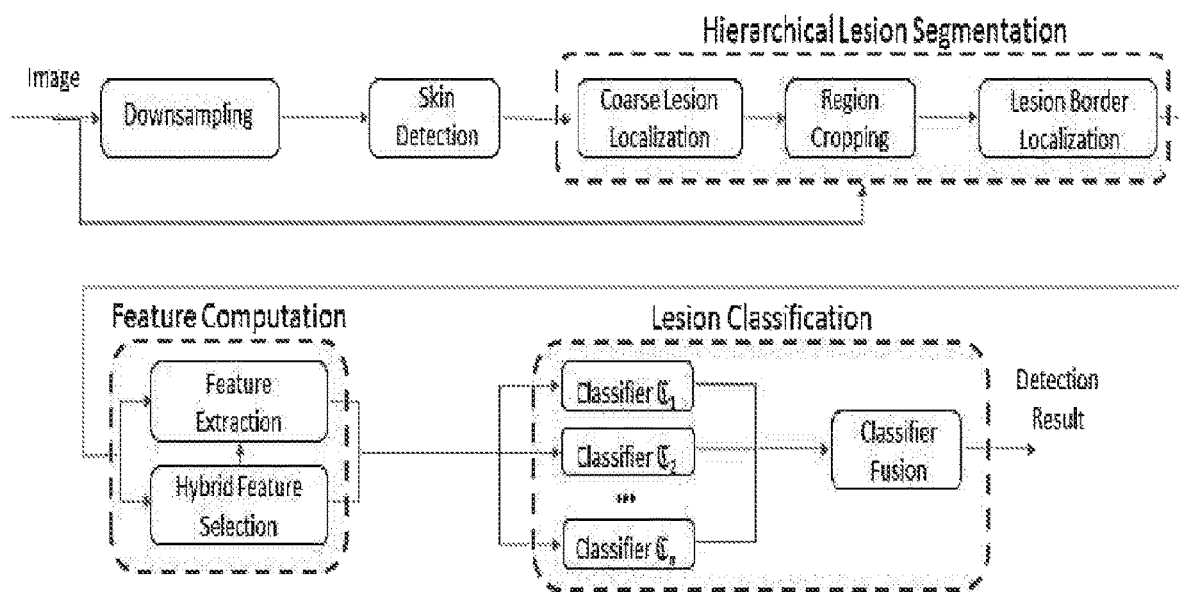
FIG. 6 is a flow chart showing the system and method according to an embodiment of the present invention.

FIG. 6 is a flowchart setting the general steps taken by the present method according to an embodiment of the present invention. The general steps are set out below:

Given a smartphone-captured skin lesion image as input, the system of the present invention performs computation to determine the likelihood of skin cancer. FIG. 6 depicts the system design with the following processing stages:

1. Pre-processing: Direct processing the smartphone-captured image is computation and memory expensive, and this exceeds the capability of mobile devices. Thus, in the preprocessing stage, the input image is downsampled, an approximate mole location is determined using the down-sampled image, and a region enclosing the mole is determined and cropped from the high-resolution input image. The approximate mole location can be determined using a minimal intra-class-variance thresholding algorithm, and/or a minimal-spanning-tree based algorithm, on the down-sampled image. The cropped region will be processed in the subsequent stages.

2. Skin mole localization: It is challenging to achieve accurate segmentation of skin lesions from smartphone-captured images under loosely-controlled lighting and focal conditions. Instead of using sophisticated but computationally-expensive segmentation algorithms, we propose to localize the skin lesion with a combination of (i) fast skin detection and (ii) fusion of two fast segmentation outputs. In particular, Otsu's method and Minimum Spanning Tree (MST) method are used to identify smoothly-changing and abruptly-changing mole borders, respectively. In the fusion processing, segments connected to boundary of skin region are removed, union of remaining segments is computed, the largest connected region is determined from the union results, and median filter is applied to the final segment.

3. Feature computation: After localizing the skin mole, we characterize it by features belonging to four feature categories: color, border, asymmetry and texture. In addition, we propose a new color feature and a new border feature:

a. New color feature: For abnormal skin lesion, its color varies nonuniform from the center to the border. We propose a new feature to capture this characteristic. The lesion is first divided into N partitions (N sectors with equal degree) and each partition is further divided into M subparts. After that, each partition is described by a M-component vector where each component is the average of pixel values of a subpart. Finally, maximum distance between the vectors quantifies the color variation. This feature is called as color triangle feature. This proposed method is computed for gray scale, red and hue channel of the lesion. Values of N are chosen from {4, 8, 12, 16}. For each value of N, values of M are chosen from {2, 4, 8}. Feature selection is used to determine the optimal parameters.

b. New border feature: We propose a new method called border fitting to quantify the irregularity of lesion border (irregular skin mole indicates abnormal condition). First, the lesion border is approximated by piecewise straight-lines. After that, the angles between every two adjacent straight-lines are computed. Mean and variance of the angles are used to characterize the border irregularity. Number of lines is chosen from {8, 12, 16, 20, 24, 28}. Feature selection is used to determine the optimal parameter.

4. Feature Selection: There are many features extracted to describe color, border or texture of a skin lesion. Likely, some are noise features. Also, redundancy between features may reduce the classification rate. Hence, a feature selection that is done in offline mode to select only good features is necessary. Only selected features will be used in the system to determine if a lesion is cancer/non-cancer. Furthermore, feature selection has an important role in our mobile-based diagnosis system, where there are strict computational and memory constraints. By using a small number of features, it will have some advantages such as reduction of feature extraction time and storage requirements, reduction of training and testing time, and reduction of the complexity of classifier. Note that it has been recognized that the combinations of individually good features do not necessarily lead to good classification performance. Finding the best feature subset with at most m features from a set of M features necessitates examining W feature subsets:

$$W = \sum_{i=1}^{m} \binom{M}{i}$$

Thus, it is hard to search for the optimal feature subset exhaustively.

The method for early melanoma detection is based upon and extends the earlier work by determining the optimal color space for the segmentation skin lesion. The method also extends the analysis and evaluation of the early MM diagnosis system. Furthermore, a set of novel features are used to better classify the skin lesion images.

It is challenging to achieve accurate segmentation of skin lesions from smartphone-captured images under loosely controlled lighting and focal conditions. Instead of using sophisticated segmentation algorithms, which can be computationally expensive, we propose to localize the skin lesion with a combination of fast skin detections and hierarchical fast segmentation.

More precisely, using a downsampled version of the skin image, a coarse model of the lesion is generated by merging different segmentation algorithms. Then, to outline the lesion contour, we employ a fine segmentation by using as input the coarse segmentation result. From the final segmented region, we extract four feature categories which accurately characterize the lesion color, shape, border and texture. To classify the skin lesion, a classifier is built for each feature category and then the final results is obtained by fusing their results.

The invention will now be described in greater detail.

TABLE I

Notations and their corresponding meanings in the description of the method

| Notations | Meaning |
|---|---|
| $\mathfrak{C}_x$ | Centroid of x, where x could be an image or ROI |
| P | The number of neighboring sampling points |
| R | The radius of neighbohood |
| $LBP_S$ | LBP sign component |
| $LBP_M$ | LBP magnitude component |
| $\mathfrak{F}$ | Feature set |
| $\mathfrak{S}$ | Selected Feature set |
| nc | The number of classes |
| n | The number of samples |
| L | Class label set |
| MI | Mutual information |
| NMI | Normalised mutual information |
| $Q_f$ | The quality of the feature f |
| H | Entropy |
| μ, σ | Mean and standard deviation |
| \|X\| | Cardinality of the set X |

Segmentation

It is challenging to achieve accurate segmentation of skin lesions from smartphone-captured images under loosely controlled lighting and focal conditions. Instead of using sophisticated segmentation algorithms, which can be computationally-expensive, the present invention first start out by localizing the skin lesion with a combination of fast skin detection and fusion of fast segmentation results. The segmentation process consists of two main steps. As a first step, a mask of skin regions is generated using skin detection method. By doing skin detection, we discard pixels from non-skin regions to simplify the image for subsequent processing step. At second step, we extract the lesion by using a combination of different segmentation methods. Our segmentation process consists of two main steps. At first step, a mask of skin regions is generated using the skin detection method. By doing skin detection, we discard pixels from non-skin regions to simplify the image for subsequent processing step. At the second step, we extract the lesion by using a hierarchical segmentation method. FIG. 1 shows the flowchart of the segmentation procedure and is described in detail below.

1. Skin Detection

The reason of doing skin detection first is to simplify the image, so an exact classification of skin and non-skin region is not needed as long as we extract a simple foreground and keep the whole lesion region inside. Here we use an approach based on skin color model to detect skin pixels [5]. First we convert the image from RGB color space into $YC_bC_r$ color space. Here we use an approach based on skin color model to detect skin pixels. We choose this particular skin model since it is more discriminative, providing 32 skin and non-skin color maps of size 64×64×64 for each skin color. We use the original RGB color image, without any preprocessing, as input to the skin detection model.

In order to build the skin detection, model we followed the steps: we first collected, from the Internet, a set of skin/non-skin images to construct our skin detection dataset. Skin images are selected with different skin colors and various lighting conditions for model generalization. The skin color distribution is estimated by a Gaussian mixture model, differently to what others have done, i.e. using an elliptical distribution. Since the skin mole we want to detect may not have the skin color full identified, we use a filling method for all the holes inside the skin region.

In an embodiment, we collect 100 skin images and 36 non-skin images from the internet to form our skin detection dataset. Skin images are selected with different skin colors and various lighting conditions. The skin color distribution is close to an elliptical distribution [11], so we detect skin pixels using an elliptical skin model on $C_bC_r$ space [5], [11]. As the skin mole we want to detect may not have skin color, we fill all the holes inside the skin region.

2. Lesion Segmentation

Since our objective is to develop a mobile-based diagnosis system, we need a lightweight segmentation method that can achieve high precision under the computation constraint, even when working on downsampled images. Therefore, as the segmentation engine we want to apply several basic segmentation methods with low computation usage (with different limitations), and then use some criteria to merge the results.

In developing a mobile-based diagnosis system, we need a segmentation method that can achieve high precision under the computation constraint. As different segmentation methods have distinct limitations, we want to apply several basic segmentation methods with low computation usage, and then use some criteria to merge the results.

After we get the skin region as the area to do our segmentation method, we perform two segmentation methods and use some rules to combine results from both methods. Here we select Otsu's method [16] and Minimum Spanning Tree (MST) method [8] to get initial segmentation results.

Otsu's method is a general histogram thresholding method that can classify image pixels based on color intensity, and it may not detect clear edges on image, for example, the lesion boundary. Otsu's method is simple and takes much less time compared to other lesion segmentation methods [10].

MST method is a fast region-based graph-cut method. It can run at nearly linear time complexity in the number of pixels. It is sensitive to clear edges but may not detect smooth changes of color intensity.

By combining the two different segmentation results, we expect to get a good segmentation on lesion with either clear border or blur border in a fast computation. Based on some rules to perform fusion of different segmentation in [10], we apply the following procedures to merge the two segmentation results. First, we remove all segments in either results that are connected to the boundary of skin region. Second, we take the union of the two results and then find the largest connected region in the union result. And last, we perform a post processing method of using median filter on the final segment to smooth the border. FIG. 2 shows results of single segmentation methods and their combination. FIG. 2(a-c) show an example where Otsu's method gives a better result than MST method. Because in this image, the lesion border is not clear, Otsu's method detects a more accurate border. FIG. 2(d-f) show an example where MST method gives a better result than Otsu's method. In this image, the lesion border is clear but the color is not uniform inside the lesion region, so MST method finds the exact border of the lesion. After we take the union from two different methods, we can get more accurate segmentation results.

Feature Calculation

1. Feature Extraction

Given the lesion image segmented described above, we examine 80 features belonging to four categories (color, border, asymmetry and texture) to describe the lesion. These features are presented in follows.

(a) Color Feature

Given a color lesion, we calculate color features widely used in the literature such as mean, variance of pixel values on several color channels. The used color channels are gray scale; red, green, blue (from RBG image); hue and value (from HSV image). To capture more color variation, we also use information from histogram of pixel values [14], [10], [2]. A histogram having 16 bins of pixel values in lesion is computed and number of non-zero bins is used as feature. This method is also applied on 6 channels mentioned above. Features achieved from these channel are called as num_gray, num_red, num_green, num_blue, num_hue and num_value.

For normal skin lesion, color varies uniformly from the center to the border. We propose a new feature to capture this characteristic. The lesion is first divided into N partitions and each partition is further divided into M subparts. After that, each partition is described by a M-component vector where each component is the average of pixel values of a subpart. Finally, maximum distance between the vectors quantifies the color variation. This feature is called as color triangle feature. This proposed method is computed for gray scale, red and hue channel of lesion. Values of N are chosen as 4, 8, 12 and 16. For each value of N, values of M are chosen as 2, 4 and 8. An illustration for proposed method is presented in FIG. 5(a). Totally, we extract 54 color features to describe the color variation.

(b) Border Feature

To describe the irregularity of border, we compute shape features such as compactness, solidity, convexity, variance of distances from border points to centroid of lesion [14].

We also propose a new method called as border fitting to quantify the irregularity of border. First, the lesion border is approximated by mean-square-error method with lines. After that, the angles between every two adjacent lines are computed. Average and variance of the angles are used to describe border irregularity. Number of lines L are chosen as 8, 12, 16, 20, 24 and 28. An illustration for proposed method is presented in FIG. 5(b). Totally, 16 features are extracted to describe the border irregularity.

(c) Asymmetry Feature

To compute the asymmetry of lesion shape, we follow the method in [2]. The major and minor axes (first and second principal components) of lesion region are determined. The lesion is rotated such that the principal axes are coincided the image (x and y) axes. The object was hypothetically folded about the x-axis and the area difference (Ax) between the two parts was taken as the amount of asymmetry about the x-axis. The same procedure was performed for the y-axis (so, we get Ay). The asymmetric feature is computed as $$\frac{Ax + Ay}{A}$$

where A is lesion area.

(d) Texture Feature

To quantify texture feature of lesion, a set of features from the Gray Level Co-occurrence Matrix (GLCM) of gray scale channel is employed. The GLCM characterizes the texture of an image by calculating how often pairs of pixel with specific values and in a specified spatial relationship occur in an image. GLCM-based texture description is one of the most well-known and widely used methods in the literature [6]. In this work, GLCM is built by considering each two adjacent pixels in horizontal direction.

Four features extracted from GLCM to describe lesion. They are contrast, energy, correlation and homogeneity. As shown in [6], to achieve a confidence estimation for features, GLCM should be dense. Hence, before GLCM calculation, the pixel values are quantized to 32 and 64 levels. It means that we computed 8 texture features from two GLCM. To capture edge information in lesion, we also use Canny method to detect edges in lesion. Number of edge pixels are counted and normalized by lesion area. This number is used as feature. Totally, 9 features are extracted to describe the texture of lesion.

2. Feature Selection

Given set F of n features and class label C, the feature selection problem is to find a set S having k features (k<n) such that it maximizes the relevance between C and S. The relevance is usually characterized in terms of Mutual Information (MI) [17], [1], [7]. Because the consideration all possible subsets having k features requires $C_n^k$ run, it is difficult for using exhausting search to find the best subset.

(a) Feature Selection Procedure

Because of above trouble, in this work, we used the well-known feature selection procedure called Normalize Mutual Information Feature Selection (NMIFS) [7] to select features. In NMIFS, at beginning, the feature that maximizes relevance with target class C is selected as first feature. Given set of selected feature $S_{m-1}$, the next feature $f_m$ is chosen such that it maximizes the relevance of $f_m$ to target class C and minimizes the redundancy between it and previous selected features in $S_{m-1}$. In other words, $f_m$ is selected such that it maximizes G function $$G(f_m) = I(C, f_m) - \frac{1}{|S_{m-1}|} \sum_{f_s \in S_{m-1}} NI(f_m, f_s) \quad (1)$$

where I is mutual information function measuring the relevance between two variables and is defined as $$I(X, Y) = \sum_y \sum_x p(x, y) \log \frac{p(x, y)}{p(x)p(y)} \quad (2)$$

NI is normalized mutual information function and is defined as $$NI(X, Y) = \frac{I(X, Y)}{\min\{H(X), H(Y)\}} \quad (3)$$

where H is entropy function 2. (From information theory, $I(X, Y) \geq 0$; $I(X, Y) < 1$ if X or Y is binary variable; $0 < NI(X, Y) < 1$)

(b) Disadvantage of MI-Based Criterion

MI usually is widely used in feature selection problem to measure the relevance between variables. However, from (2), we observed that MI is a measure based on the probability functions. It is independent to coordinate of variable values which may be useful in classification context. For examples, in two categories classification, suppose that number of samples in each category are equal and there are two features $f_1$, $f_2$ which perfectly separate two categories. By Vapnik-Chervonenkis theory [21], the feature has larger margin between two categories will give a better generalization error. Hence, it should be better than another feature. However, by using MI, it is easy to show that these features will have same MI value with class label (C) which equals to 1. A well-known criterion considering the coordinate of features is Fisher criterion (F-test). However, there are some disadvantages of Fisher criterion figured out in [9]. Fisher criterion may not be good incase (i) the distribution of the data in each class is not a Gaussian; (ii) mean values of classes are equal/approximate.

(c) New Feature Selection Criterion

To overcome drawback MI-based criterion, we propose a new criterion taking into account the feature coordinate when evaluating the goodness of features. The general idea of our new criterion is inspired from the work of Wang et al. [23] in face recognition problem. In that work, authors defined a new transformation called "Average Neighborhood Margin (ANM) maximization" which pulls the neighboring images of the same person towards it as near as possible, while simultaneously pushing the neighboring images of different people away from it as far as possible. We adapt the general idea to the feature selection problem and propose a goodness of feature f defined as $$M(f) = \sum_{i=1}^{N} \left\| \sum_{k \in N_i^e} \frac{\|f(i) - f(k)\|_1}{N_i^e} - \sum_{j \in N_i^o} \frac{\|f(i) - f(j)\|_1}{N_i^o} \right\| \quad (4)$$

where N is number of data points (samples); for each sample i, $N_i^o$ is the set of the most similar samples which are in the same class with i; $N_i^e$ is the set of the most similar samples which are not the same class with i; f(i) is feature value of $i^{th}$ sample. Eq. (4) means that a feature is good if each sample is far from samples belonging other classes while it is near to samples belonging same class. Because ANM criterion uses only local information and does not make any assumptions on the distributions of samples, ANM can overcome drawbacks of Fisher criterion.

Finally, to take advantages both MI and ANM, we propose a new feature criterion which replaces G function in eq. (1) by the following function $$G(f_m) = \alpha * \underset{\text{Margin}}{M(f_m)} + (1-\alpha) * \left[ \underset{\text{Relevance}}{I(C, f_m)} - \frac{1}{|S_{m-1}|} \sum_{f_s \in S_{m-1}} \underset{\text{Redundancy}}{NI(f_m, f_s)} \right] \quad (5)$$

where $\alpha \in [0, 1]$ is weight that regulates to the importance of ANM. Note that M is normalized to [0, 1] before computing eq. (5).

Results and Discussion

The database includes 81 color images provided by National Skin Center, Singapore. Number of cancer and non-cancer images are 29 and 52, respectively.

The segmentation process described above is applied on these images to extract lesion regions. After that, 80 features belonging four categories (54 color features, 16 border features, 1 asymmetric feature and 9 texture features) as described in earlier sections above are extracted to describe each lesion region. These features are normalized by z-score before subjecting to feature selection step. To compute mutual information between features, features should be first discretized. To discretize each feature, the interval [μ−2σ, μ+2σ] is divided into k equal bins; where μ, σ are mean and standard deviation of feature. Points falling outside the interval were assigned to extreme left or right bin. From suggestion in [18], k should be 1<k<5. We run feature selection with k=2, 3, 4, 5. The best classification accuracy shown in next section is achieved at k=5. Values of $N_i^o$ and $N_i^e$ in eq. (4) are set to 50% number of samples of class containing $i^{th}$ sample. α in eq. (5) is set to 0.4.

Because all color, border, asymmetry and texture have important role in judging a lesion, we apply feature selection for each category of features. For each feature category, we select the subset of features giving highest classification accuracy. Feature selection is not necessary to apply asymmetric category because only one asymmetric feature is extracted. After achieving the feature subsets for each category, a SVM classifier [3] is trained for each subset. In testing stage, for each feature subset, the corresponding SVM is used to make a prediction. The output of SVM will be 1 (cancer) or 0 (non-cancer). Here, we use 5-folds cross validation for training and testing. To combine results of four classifiers, we sum their outputs (sum-rule). A lesion is judged as cancer if sum value is larger than 1.

As an example, FIG. 3 shows how the specific features of color variation and border irregularity is characterised and quantified. For abnormal skin lesion, its color varies non-uniformly from the center to the border. With this invention, we propose a new feature to capture this characteristic. With reference to FIG. 3(a), the lesion is first divided into N partitions (N sectors with equal degree) and each partition is further divided into M subparts. After that, each partition is described by a M-component vector where each component is the average of pixel values of a subpart. Finally, maximum distance between the vectors quantifies the color variation. This feature is called as color triangle feature. This proposed method is computed for gray scale, red and hue channel of the lesion. Values of N are chosen from {4, 8, 12, 16}. For each value of N, values of M are chosen from {2, 4, 8}. Feature selection is used to determine the optimal parameters.

In addition to the above, we also propose a new method called border fitting to quantify the irregularity of lesion border (irregular skin mole indicates abnormal condition). With reference to FIG. 3(b), the lesion border is first approximated by piecewise straight-lines. After that, the angles between every two adjacent straight-lines are computed. Mean and variance of the angles are used to characterize the border irregularity. Number of lines is chosen from {8, 12, 16, 20, 24, 28}. Feature selection is used to determine the optimal parameter.

Feature Selection Results

TABLE I

|  | MI-based criterion | Our criterion |
|---|---|---|
| color | num hue, color triangle (red channel, N = 16, M = 8), num red, num green | num hue, color triangle (red channel, N = 16, M = 8), num value |
| border | mean of border fitting (L = 28) | variances of border fitting (L = 28, L = 8) |
| asymmetry |  | (Ax + Ay)/A |
| texture | correlation of GLCM (32 levels quantization), number of edge pixels, contrast of GLCM (64 levels quantization) | |

Table I shows selected features in each category when MI-based criterion and our criterion are used in feature selection. The classification accuracy is given in Table II.

TABLE II

| | MI-based criterion | | | | | Our criterion | | | | |
|---|---|---|---|---|---|---|---|---|---|---|
| | color | border | asymmetric | texture | combine | color | border | asymmetric | texture | combine |
| non-cancer | 94.00 | 82.55 | 92.36 | 84.55 | 90.18 | 94.18 | 79.27 | 92.36 | 84.55 | 90.55 |
| cancer | 86.00 | 66.00 | 33.33 | 76.67 | 90.00 | 90.00 | 76.00 | 33.33 | 76.67 | 96.67 |
| average | 90.00 | 74.27 | 62.85 | 80.61 | 90.09 | 92.09 | 77.64 | 62.85 | 80.61 | 93.61 |

For texture features, feature selection using MI-based criterion and our criterion give same best feature subset. The highest accuracy is 80.61% when 3 features are selected.

FIG. 4(a) shows the classification accuracy with different number of selected color features. The MI-based criterion achieves highest accuracy 90% when number of selected features equals 4. The highest accuracy of proposed criterion is 92.09% when number of selected features is only 3.

From Table I, we can see that color triangle features always appear in selected features for both MI-based criterion and our criterion. This confirms the efficiency of proposed color triangle features. We also see from this table that number of non-zero bins of histogram are a good feature to capture color variation.

FIG. 4(b) shows the classification accuracy with different number of selected border features. The MI-based criterion achieve highest accuracy 74.27% when only one feature is selected. By using MI-based criterion, we have no chance to get a higher accuracy even more features are added. The highest accuracy of proposed criterion is 77.64% when 2 features are selected. From Table I, we can see that border fitting features are selected features for both MI-based criterion and our criterion. This confirms the efficiency of proposed border fitting features.

Table II also shows the accuracy when four classifiers corresponding to 4 feature categories are combined by sum rule. When combined, our criterion outperforms MI-based criterion. The average accuracy of MI-based criterion and our criterion are 90.09% and 93.61%, respectively. Our criterion also achieves a high accuracy (96.67%) for cancer samples. It is important in practice where a high accuracy detection for cancer is required.

Mobile Implementation

Because the image taking from mobile may have a big size, the image will be resized to a lower resolution for reducing time processing and memory to store image. After lesion segmentation, 9 selected features (by our criterion, table I) including 3 color features, 2 border features, 1 asymmetric feature and 3 texture features will be extracted to describe that lesion. These features will be subjected to corresponding SVM classifiers. The results from 4 SVM classifiers will be combined by sum rule to give final score. The final score is in the interval [0,4]. A high score means high cancer risk. The average processing time for each image on a Samsung Galaxy S4 Zoom (CPU: Dual-core 1.5 GHz, RAM: 1.5 GB, Camera: 16 Mp) is less than 5 seconds. The screenshot mobile application is shown in FIG. 5.

EXAMPLE 2

Lesion Segmentation

Our segmentation process consists of two main steps. At first step, a mask of skin regions is generated using the skin detection method. By doing skin detection, we discard pixels from non-skin regions to simplify the image for subsequent processing step. At the second step, we extract the lesion by using a hierarchical segmentation method.

Skin Detection:

The reason of applying a skin detection procedure first is to filter the image from unwanted artifacts, so an exact classification of skin/non-skin regions are not needed as long as we extract the foreground and keep the whole lesion region within. Here we use an approach based on skin color model to detect skin pixels. We choose this particular skin model since it is more discriminative, providing 32 skin and non-skin color maps of size 64×64×64 for each skin color. We use the original RGB color image, without any preprocessing, as input to the skin detection model. In order to build the skin detection, model we followed the steps: we first collected, from the Internet, a set of skin/non-skin images to construct our skin detection dataset. Skin images are selected with different skin colors and various lighting conditions for model generalization. The skin color distribution is estimated by a Gaussian mixture model, differently to what others have done, i.e. using an elliptical distribution. Since the skin mole we want to detect may not have the skin color full identified, we use a filling method for all the holes inside the skin region.

Hierarchical Lesion Segmentation:

Since our objective is to develop a mobile-based diagnosis system, we need a lightweight segmentation method that can achieve high precision under the computation constraint, even when working on downsampled images. Therefore, as the segmentation engine we want to apply several basic segmentation methods with low computation usage (with different limitations), and then use some criteria to merge the results.

The skin lesion images are converted the grayscale color space for the rest of the hierarchical segmentation.

a) Coarse Lesion Localization:

There are several common methods used to perform lesion segmentation: histogram thresholding, clustering, edge-based, region-based, and active contours. Histogram thresholding use image histogram to determine one or more intensity values for separating pixels into groups. The most popular thresholding method for lesion segmentation is Otsu method, which is based on the maximum variance.

After getting the skin region area, to do our segmentation method, we downsample the image and perform two segmentation methods, and use some rules to combine the results of both methods. Here we select Otsu's method and Minimum Spanning Tree (MST) method to get the initial segmentation results. FIG. 1(b) shows the flowchart of the coarse lesion localization procedure.

Otsu's method is a general histogram thresholding method that can classify image pixels based on color intensity, and it may not detect clear edges on image, for example, the lesion boundary. Otsu's method is simple and takes much less time compared to other lesion segmentation methods. On the other hand, the MST method is a fast region-based graph-cut method. It can run at nearly linear time complexity in the number of pixels. It is sensitive to clear edges but may not detect smooth changes of color intensity. The parameters of the MST were adjusted such that we could get enough candidate ROIs while avoiding over-segmentation near the skin mole region. Here we use an efficient MST algorithm that can run at nearly linear time complexity in the number of pixels. Therefore, we can achieve a low time complexity after running two different segmentation methods. To filter the segmentation results of the Otsu and MST, we firstly remove all candidate ROIs that are connected to the boundary of skin image. In addition, we assume that the skin mole is located in a region (called the valid region) near the center of the image. This hypothesis was adopted since most of the users focus their camera phone on the object of interest (i.e., the skin mole) when capturing a picture. As a consequence, all the candidate ROIs that have the centroid coordinates outside the valid region are discarded.

Figure 7:
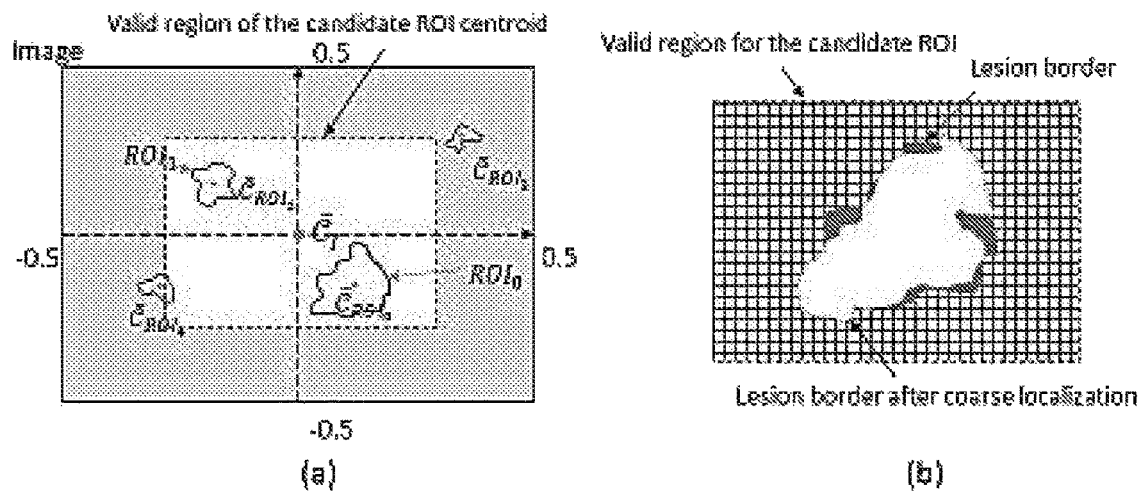
FIG. 7 shows two main concepts of the hierarchical segmentation: (a) the valid region of the ROIs together with the constraint used during the localization process and (b) the uncertainty problem of the border localization for a synthetic ROI.

Finally, we impose a constraint to further discard the noisy ROIs which is defined as $$\operatorname{argmax}_i \{A_i \cdot (1 - 2 \cdot \sqrt{(C^x_i)^2 + (C^y_i)^2})^4\}, i = 1, \ldots, n_{ROI} \quad (1)$$

where, for the $i^{th}$ ROI, $A_i$ denotes its area, and $C^x_i$ and $C^y_i$ are centroid coordinates (x and y). $n_{ROI}$ represents the total number of ROIs that are located in the valid region. The basic idea is to give central mole regions very high weights while penalizing mole regions near to boundary. When both x and y coordinates of the mole centroid are close to the image center, then [equation] is close to 1. The power 4 in the formula decide the penalty. FIG. 7(a) shows the valid region for the ROIs and the constraint used in the localization process. By merging the two filtered segmentation results, we expect to get a good segmentation on lesion with either clear border or blur border. Based on some rules to perform fusion of different segmentation in, we take the union of the two results and then find the largest connected region in the union result. The fused segmentation result is post processed by applying a median filter to remove the noise.

b) Border Localization:

To locate the candidate region of interest (ROI) for the lesion, the coarse segmentation algorithm is applied in the first instance on the low-resolution image acquired by the mobile device, due to scars resources. In the second phase, after we obtain an approximate location of the lesion, using the low-resolution image as reference, we crop the corresponding ROI from the original high-resolution image. Since downsampling is a nonlinear operation, this mapping is not exact and generates an uncertainty related to contour localization. The border of a synthetic ROI, obtained after applying the coarse lesion segmentation, together with the actual contour are illustrated in FIG. 7(b).

Thus, another fine grain segmentation operation is preformed to improve the lesion border localization. The segmentation algorithm adopted for this stage is similar with the one presented in the previous section, except that we adapt the segmentation parameters to the cropped image characteristics, i.e., a skin image containing a mole which occupies a large part of the image. Furthermore, the ROI image is enlarged by adding a fixed number of extra pixels, from the original image, on each side of it.

B. Feature Descriptors for Describing Lesion

Given the lesion image segmented from above, we compute features belonging to four categories (color, border, asymmetry and texture) to describe the lesion. The summary of features is given in table below. Detail of features are presented in the follows.

| Feature Category | Used Features |
|---|---|
| LCF | Mean, standard deviation, skewness, and kurtosis of different color spaces (RGB, HSV and grayscale). |
| | Number of non-zero bins of the histograms of different color spaces (RGB, HSV and grayscale). |
| | Color Triangle feature. |
| LBF | Shape feaures such as compactness, solidity, convexity |
| | variance of distances from lesion border points to the lesion centroid. |
| | Border Fitting feature. |
| LAF | Shape asymmetry. |
| LRF | Edge density. |
| | Features computed from the GLCM like energy, correlation, contrast, entropy. |
| | Rotation invariant sign and magnitude of LBP of different color spaces (RGB and grayscale). |

1) Lesion Color Feature (LCF) (54 Features):

Given a skin lesion, we calculate the color features widely used in the literature such as mean, variance of the pixel values of several color channels. The used color channels were red, green, blue from the RGB image; gray scale from the gray image (FIG. 8a, 8d); and hue and value from the HSV image (FIG. 8b, 8e). To capture more color patterns from the skin lesion, we use the information from the histogram of pixel values. A histogram, with fixed number of bins, of the pixel values in lesion is computed and the number of non-zero bins is used as the discriminative feature [FIG. (8g), (8h), (8i), (8j)]. The features generated from the color channels are called num_red, num_green, num_blue, num_gray, num_hue and num_value.

Generally, there is a different color distribution pattern over the MM lesion whereas the normal pigmented nevi exhibit a more color representation. Therefore, another measurement is needed to find out if there is a color variation all over the lesion or the color varies uniformly from the center to the border. Inspired by the clinical research, we propose another feature called Color Triangle (CT). To measure CT, the lesion is first divided into PA partitions and each partition is further divided into SP subparts. After that, each partition is described by a SP-component vector, where each component is the mean pixel values of a subpart. Finally, the maximum distance between the partitions vectors quantifies the color variation of the skin lesion.

We compute this feature for grayscale, red and hue channels of the lesion. Based on the above description, the CT is computed as $$CT = \max \|v_i - v_j\|2, i, j = 1, \ldots, PA \quad (2)$$

where $v_i$ is the vector describing the $i^{th}$ partition.

FIG. (8c) and FIG. (8f) show the benign and MM skin lesions partitioned, by black lines, into regions and subparts. As shown in the figures, the color variation is higher for the MM than the benign case, due to the growth patterns of the lesions.

2) Lesion Border Feature (LBF) (16 Features):

To describe the irregularity of the border, we compute shape features such as compactness, solidity, convexity, and variance of distances from border points to centroid of lesion. We also propose a new feature, called Border Fitting, to quantify the border irregularity. The main idea is to approximate the lesion contour points by lines and then to calculate the angle between these lines. Regular borders tend to have smooth changes without significant modifications between consecutive data points, compared with irregular ones.

We use a linear regression model to measure the estimation error from the border pattern, such that discriminative features of irregularity of the contour change can be extracted. Assume that the contour points of the lesion are grouped into nt segments and $x_i$ is the corresponding coordinate for the segment line i. In the linear regression, the predicted coordinate $\hat{y}_i$ can be expressed as $\hat{y}_i = a^i_0 + a^i_1 \cdot xi$, where $a^i_0$ and $a^i_1$ are the slope and intercept of the regression line.

The estimation error $yi - \hat{y}_i$, in terms of root mean-square-error, is the difference between the predicted coordinates of the segment line and the true coordinates.

The estimation error $yi - \hat{y}_i$, in terms of root mean-square-error, is the difference between the predicted coordinates of the segment line and the true coordinates. The average and variance of the angles between every two adjacent lines are used as the border irregularity features.

Lesion Asymmetry Feature (LAF) (1 Feature):

The lesion asymmetry can also reveal valuable information for the lesion categorization. To compute the lesion asymmetry, we use a method similar to the one introduced in. The major and minor axes of lesion region, i.e., the first and second principal components, are determined. The lesion is rotated such that the principal axes are coincided with the image axes x and y. The object was hypothetically folded to the x-axis and the area difference i.e., A, between the two parts was taken as the amount of asymmetry corresponding to the x-axis. We followed the same procedure, for the y-axis, to obtain $A_y$. The asymmetric feature is computed as $A_{sym} = (A_x + A_y)/A$, where A is the lesion area.

Lesion Texture Feature (LTF) (45 Features):

To quantify the texture of the skin lesion, we investigated several feature descriptors such as: those dervided from the gray level co-occurrence matrix (GLCM) and those based on the local binary patterns (LBP).

The GLCM of the entire lesion characterizes the texture by calculating how often pairs of pixel with specific brightness values and orientation occur in an image. GLCM-based texture description is one of the most well-known and widely used methods in the literature.

In this work, GLCM is constructed by considering each two adjacent pixels in the horizontal direction. The features extracted from GLCM used to describe the lesion are contrast, energy, correlation and homogeneity. To achieve a reasonable estimation of the features, the GLCM should be a dense matrix. Hence, before GLCM calculation, the pixel values are quantized to 32 and 64 levels. It means that we computed 8 texture features from two quantized GLCMs.

To capture edge map (structure) of the lesion, we employed the Canny edge detector method. The number of edge pixels are counted and normalized by total lesion area and the resulted number is used as an edge density feature. Another widely used texture descriptor that we employed for skin lesion analysis is LBP, which has shown promising results in many computer vision application. LBP combines shape and statistical information by a histogram of LBP codes which resemble to microstructures in the image at various scales. The LBP is a scale invariant measure that describe the local structure in a 3×3 pixel block. The operator was further adapted to accommodate arbitrary block sizes, rotation invariance and multiresolution. We adopt the LBP framework introduced in since it has a complete mathematical formulation of the LBP operator and it has been extensively tested, offering best performance. In a nutshell, it has been proposed that a full characterization of the local pattern in terms of the sign (S), magnitude (M) and central pixel (C). The sign LBP (LBPS), which is actually the original LBP operator, is determined by computing the local binary difference between the gray value of a pixel x and the gray values of P pixels in a local neighborhood of x placed on a circle of radius R:

$$\begin{cases} LBP_S(x, R, P) = \sum_{i=1}^{P} 2^i \mathcal{H}(I(x_i) - I(x), 0) \\ x_i = x \cdot \left[ R \cdot \sin\left(\frac{2\pi i}{P}\right), -R \cdot \cos\left(\frac{2\pi i}{P}\right) \right]^T \\ \mathcal{H}(y, 0) = \begin{cases} y, & x \geq 0 \\ 0, & x < 0 \end{cases} \end{cases} \quad (3)$$

where I denotes the image, H(•) is the Heavidside function and $x_i$ are P sample pixels around x at distance R. The magnitude LBP ($LBP_M$), is defined as follows:

$$\begin{cases} LBP_M(x, R, P) = \sum_{i=1}^{P} 2^i \mathcal{H}(I(x_i), m_I) \\ m_I = \text{mean}(I) \end{cases} \quad (4)$$

where mean(I) is the average value over the entire lesion image. We extracted the LBPS and LBPM from the grayscale channel and red channel of the RGB lesion image.

To generate a rotation invariant (ri) LBP and $LBP_M$, P−1 bitwise shift operations of the circle (i.e., a ri map) are performed, and the smallest value is selected. In order to characterize the ROI image, for each component of the LBP descriptor a feature histogram is generated that is measured with different radii for multiscale analysis. The dimensionality of the LBP features is closely related to the image size, the R and P parameters and the used mapping, e.g., for a sample image of size 256×256, and ri map with R=1 and P=8 475 the resulting length of $LBP_S$ (or $LBP_M$) is 36.

C. Feature Selection

Given the feature set F and the class label L, the feature selection problem is to find a set $G \subset F$ ($|G|<|F|$) such that it maximizes the relevance between L and G. The relevance is usually characterized in terms of Mutual Information (MI). Considering all possible feature subsets requires an exhaustive search which is not recommended for a large feature set.

In this work we turned our attention to the well-known feature selection procedure called Normalize Mutual Information Feature Selection (NMIFS). Mutual information is widely employed for the feature selection problem to capture the relevance between variables. For instance in NMIFS, initially the feature that maximizes relevance with target class L is selected as the first feature. Given the set of selected feature $G=\{f_s\}$, $s=1, \ldots, |G|$, the next feature $f_i \in F\backslash G$ is chosen such that it maximizes the relevance of $f_i$ with the target class L and minimizes the redundancy between it and the selected features in G. In other words, $f_i$ is selected as such that it maximises the following condition:

$$\operatorname*{argmax}_{f_i} \left\{ MI(L, f_i) - \frac{1}{|G|} \sum_{f_s \in G} NMI(f_i, f_s) \right\} \quad (5)$$

Where MI is the mutual information, which measures the relevance between two random variables X and Y and is defined as $$MI(X, Y) = \sum_x \sum_y p(x, y) \log \frac{p(x, y)}{p(x)p(y)} \quad (6)$$

While NMI is the normalised mutual information and is defined as $$NMI(X, Y) = \frac{MI(X, Y)}{\min\{H(X), H(Y)\}} \quad (7)$$

where H is the entropy. From information theory, it is known that $MI(X,Y) \geq 0$; if X or Y is binary variable then $MI(X,Y) \leq 1$; and we always have $0 \leq NMI(X,Y) \leq 1$.

From (6) we observe that mutual information is a metric that relies on the probability functions, and it is independent to the coordinate of variables which may help in classification context. For example, in a binary classification problem, suppose that the number of samples in each class are equal and there are two features $f_1$ and $f_2$ which perfectly separate the two classes. The feature that has a larger margin between two classes will give a better generalization error. But, by using mutual information, it is easy to see that these features will generate the same MI value. To prevail the limitations of the mutual information criterion we thought take into consideration the features coordinates when evaluating their discrimination power. A well-known criterion considering the coordinate of features is Fisher criterion (F-test). Nevertheless, there are several issues with Fisher criterion which will cause it to fail if the data in each class does not follow a Gaussian distribution and the mean values of the classes are equal or approximate. As a consequence, we propose a new criterion taking into account the feature coordinate when evaluating the goodness of features. This is similar to a transformation called "Average Neighborhood Margin (ANM) maximization" is defined, which pulls the neighboring images of the same person towards it as near as possible while simultaneously pushing the neighboring images of different people far away. We adapted this idea to the feature selection problem and defined the quality of feature f as $$Q(f) = \sum_{i=1}^n \left\| \left( \sum_{t \in n_i^e} \frac{\|f(i)-f(t)\|_1}{n_i^e} - \sum_{j \in n_i^o} \frac{\|f(i)-f(j)\|_1}{n_i^o} \right) \right\|_1 \quad (8)$$

where, for each sample i, $n_i^o$ is the set of the most similar samples which are in the same class with i and $n_i^e$ is the 536 set of the most similar samples which are not in the same class with i. In (8) a feature has good discriminative power if we can used it to separate each sample from the samples belonging other classes whilst it is close to samples belonging to the same class, Since ANM make use of local information and does not make any assumptions on the distributions of samples it can overcome the drawbacks of the Fisher test.

Furthermore, to take advantage of MI, we combine the both ANM and MI in a single unified criterion defined by the following relation $$U(f_i) = \alpha \cdot Q(f_i) + (1 - \alpha) \cdot MI(L, f_i) - \frac{1}{|G|} \sum_{f_s \in G} NMI(f_i, f_s) \quad (9)$$

Where $\alpha \in [0,1]$ is a weight factor that control the influence of ANM and MI in the proposed hybrid criterion. Note that, in order to have the same scale, we normalise Q to [0,1] before computing (9).

D. Classifier

After the feature selection process, features from each category are fed into a binary class SVM classifier. To fuse the SVM results of the four classifiers, we sum their outputs. We choose this fusion rule due to the fact that is simple, and weights the contribution of each feature category equally during the diagnosis decision. A skin lesion is judged as cancer if the sum of SVM's output values is greater than 1.

For the LBP features we use a different classifier. The k nearest neighbor classifier (kNN) is applied for classification of majority of LBP descriptors since is a good candidate when working in a distance representation of objects. Furthermore, since LBP produces a high dimensional feature vector 563 we will require a large number of samples in order to project the LBP features to higher space where we can use SVM. As a consequence, we adopt kNN with the distance metric between two images being a pooled histogram difference between feature histograms. Each ROI image (segmented skin mole) is denoted by a set of feature histograms. Dissimilarities between ROIs are expressed as dissimilarities between the feature histogram:

$$D_{ROI}(B_i, B_j) = \sum_{h=1}^n D(E_h(B_i), E_h(B_j)) \quad (10)$$

where are $B_i$ and $B_j$ are the ROIs of two skin moles, $E_h$ denotes the corresponding feature histograms and D is the dissimilarity metric. In general, several metrics have been employed to classify the LBP histograms such as, negated histogram intersection, chi-square distance, L1 distance and cosine distance. In this study we decided to adopt the cosine distance metric for the kNN classifier since it is more robust to outliers and it was widely used in many previous works.

E. Iterative-Based Design

Compared with studies on self-monitoring applications (e.g. apps for quantified-self, device for monitoring health), studies on self-diagnosis applications have two main challenges: difficult for field study without investigating the human factors and psychological engagement.

To design a suitable interface for our proposed algorithm we resort to a two rounds study. The first round is a "Wizard-Of-Oz" task consisting of three diseases diagnosis, which was used to engage participants into the real self-diagnosis scenarios without limiting to one disease. The second session is an exploratory study based on a prototype that implements our mobile skin cancer self-diagnosis algorithm. After participants completed the first round, we presented the prototype to them and illustrated the design ideas that we had already incorporated or may want to incorporate.

Results and Discussion

1. Dataset

The datasets used in this Example 2 to evaluate the proposed scheme come from the National Skin Center (NSC) of Singapore, and consist of 184 (for the dataset called SET1) and 81 (called SET2, which is a subset of SET1) color images of skin mole lesions acquired by a professional photograph using a digital camera under different resolutions and sizes. Some of these images are challenging for the segmentation and classification due to the acquisition conditions (such as lightning and focus) and the presence of other anatomical features (e.g, eye, eyebrow, nail, etc.) near the skin lesion.

The image dataset SET1 is classified into two classes: benign nevus (117 images) and MM (67 images). The distribution of the classes for SET2 is benign nevi: 52 images, and MMS: 29 images. This small dataset was used entirely as the working data for the feature selection phase. Melanoma class is further subdivided into acral lentiginous melanoma (ALM) and non-ALM. ALM are malignant skin lesions mostly found on palms, soles, under the nails and in the oral mucosa. There are a total number of 36 ALMs in the experimental dataset SET1. The diagnosis of the melanoma cases were determined by histopathological examination or clinical agreement by several expert dermatologists from NSC. In order to obtain the ground truth (GT) ROI for each skin lesion an expert was used to manually annotate them.

To standardize the range of the computed features we normalize them using the z-score: z-score=$(f-\mu)/\sigma$, where $\mu$ and $\sigma$ represent the mean and standard deviation of feature vector f for the entire dataset. The multiclass SVM model is devised by using a radial basis 628 function (RBF) kernel. The kernel function of the SVM model is optimized by the using grid search technique performed on 630 a dataset of randomly selected 25 samples from SET1 (15 benign nevi and 10 MMs). In grid search, optimal values of kernel parameters (i.e., the cost and the free parameter SVM) are obtained by selecting various values of grid range and step size. The initial values employed during the gird search, for the feature selection, were: 5-fold cross-validation accuracy; step size for the gird search, stepSize=1; the cost, $C_{SVM}$=5; $\gamma_{SVM}$=1=#(of features), i.e. $\gamma_{SVM}$=1/79=0:0126. After obtaining the best values of the SVM parameters, for the feature selection, we performed a 5-fold cross-validation on SET2 by setting the additional parameters, such as maximum number of iteration to 1000 and the tolerance of the termination criterion to $10^{-6}$.

The performance of the classifiers on SET1 and SET2 (which are imbalanced datasets) is calculated in terms of sensitivity (i.e., Sens=TP/(TP+FN)), specificity (i.e., Spec=FN/(FN+FP)) and balanced accuracy (i.e., Acc= (Sens+Spec)/2).

2. Segmentation Results

The hierarchical segmentation process is applied on the SET1 to extract lesion ROIs. All the images that have one of their edge size greater than pixels were downsampled, while preserving they aspect ratio, using cubic interpolation with anti-aliasing. During the lesion border localization, the value of extra pixels (i.e., EXT) added on every side of to the ROI was set to 300 pixels. Otsu segmentation does not have any parameter to set since its automatically tunes the optimal thresholding value.

Instead, the performance of MST heavy relies on the chosen parameters. The optimal MST parameters for the downsampled SET1, obtained after a grid search, were: the standard deviation used by the Gaussian filter=1:2, minimum component size min_MST=20, and k_MST=800.

To measure the boundary segmentation results we used the true detection rate (TDR), which quantifies the rate of pixels classified as lesion. The TDR is computed as follows:

$$TDR(GT, SEG) = 100 \cdot \frac{\#(GT \cap SEG)}{\#(GT)} \quad (11)$$

where SEG (a binary image) denotes the result of the proposed segmentation method and GT (a binary image) denotes the ground truth segmentation. FIG. 9 shows the segmentation results for two MM lesions. These are difficult cases where one of the algorithm fails (Otsu in FIG. 9(b), whilst MST in FIG. 9(c)) to localize the lesions ROI. The melanoma lesion shown in FIG. 9(a), FIG. 9(c) and FIG. 9(e) contains regions with different visual features located near the border. Furthermore, the illumination conditions change the color pattern of the skin and mole. This image was well segmented only by the Otsu method (FIG. 9(a)), while MST got trapped in one of the border regions of different color intensity.

For the MM displayed in FIG. 9(b), FIG. 9(d), and FIG. 9(f) the MST method was able to accurately locate its center part (FIG. 9(d)) while Otsu method fails entirely (FIG. 9(b)). It is worth pointing out that, this MM image has pronounced contour irregularities, "bumpy" structure and two distinct parts: the central region which is wound-like lesion with slough/necrotic tissue and the region that comprises the gray/black margins. However, by using the proposed method we can determine the lesion boundary when one of the segmentation methods fails. The candidate color channels tested for the segmentation were the red channel of the RGB image and the grayscale (i.e., Gray=R 0:299+G 0:587+G 0:114).

C. Feature Selection Results

The novel feature selection tool is employed on the feature categories, i.e., 54 color features, 16 border features and 9 texture features. It is worth to point out that we have not applied the feature selection for the asymmetry category (since it contains only one feature) and LBPS due to the fact is already in a condensed binary format. In addition, to be able to apply the feature selection on the high dimensional LBP descriptors and learn the most dominant patterns we will require a large dataset which we were not able to obtain.

In order to compute mutual information, features should be first discretized. To discretize each feature, the original interval is divided into a number of equal bins. Points falling outside the interval are assigned to extreme left or right bin. We run feature selection with the number of bins equal to {2, 3, 4, 5}. The best classification accuracy is achieved for the number of bins equal to 5.

The values of $n^o_i$ and $n^e_i$ in (8) are set to 50% number of samples of class containing the sample i, and in (9) is set to 0:4. For the CT feature the number of partitions considered are PA={4, 8, 12, 16}, while the number of subparts are SP={2, 4, 8}. For the Border Fitting feature the number of lines analyzed was nt={8, 12, 16, 20, 24, 28}.

Since all color, border and texture features have important role in judging a skin lesion, we decide to apply the feature selection procedure for each category of features, i.e., within each category we select the subset of features giving highest classification accuracy. Table III shows selected features in each category when MI-based criterion and our criterion are used during the feature selection. The classification accuracy of different feature categories for MI-based criterion and our criterion is given in table IV.

TABLE III

Selected features from each category when mutual information criterion and our criterion are used.

| Feature Category | Mutual Information | Proposed |
|---|---|---|
| color | num_red, color triangle (SP = 16, PA = 8), num_hue, num_green | num_gray, color triangle (SP = 16, PA = 8), num_hue |
| border | mean of border fitting (for nt = 12) | variances of border fitting (for nt = {8, 12}) |
| texture | edge density contrast of GLCM (64 quantization levels) correlation of GLCM (32 quantization levels) | |

TABLE IV

The classification performance when MI-based criterion and our criterion are used for feature selection. The Sens, Spec and balanced Acc are computed for each feature category. For the texture category, we use a combination of the GLCM-based and edge density features. The values in bold correspond to the best performance.

| | | Feature Selection Criterion | | | | | |
|---|---|---|---|---|---|---|---|
| | | Mutual Information | | | Proposed | | |
| | | Feature category | | | | | |
| | | color | border | texture | color | border | texture |
| SET2 | Sens | 94.00 | 82.55 | 84.55 | 94.18 | 79.27 | 84.55 |
| | Spec | 86.00 | 66.00 | 76.67 | 90.00 | 76.00 | 76.67 |
| | Acc | 90.00 | 74.27 | 80.61 | 92.09 | 77.64 | 80.61 |

The mutual information criterion achieves highest accuracy 90% when number of selected color features equals 4. The highest accuracy of proposed criterion is 92:09% when number of selected features is only 3. From table III, we can see that CT feature always appears among selected features which confirms the efficiency of proposed feature. The mutual information criterion achieves highest accuracy 74:27% when only one border feature is selected. By using mutual information criterion, we cannot get a higher accuracy even more border features are added. Instead, the highest accuracy of the proposed criterion is 77:64% when 2 border features are selected. From table III, we can see that Border Fitting feature are selected for both criterions. This demonstrate the efficiency of proposed features.

D. Classification Results

Since the ROIs are color images we applied the LBP-based texture descriptor on both the red channel and on the converted grayscale image. Furthermore, we resized the ROIs to 256×256 pixels using cubic interpolation with anti-aliasing enabled. The ROIs images, without any pre-processing (such as noise removal), were used by the LBP-based feature extraction pipeline. For the LBP we considered the following number of samples, radii and mapping: R={1, 2}, P={8, 16} and map=ri. Common parameter considered for the LBP is the number of neighbors for the kNN classifier, i.e., k={1, 2, 3}.

After a grid search we noticed that for the multiscale LBP the size of the feature vector is much larger while the gain in accuracy is not significant. Furthermore, concatenating LBPS and LBPM does not improve the classification accuracy (even for the multiscale case) and better results are obtained when using the grayscale ROIs. We observed that the tendency is to use small scale, i.e., R=1 and P=8, and rotation-invariant features instead of uniform or rotation uniform features. Therefore, the optimal parameters that we selected were: k=2, R=1 and P=8 and the grayscale channel.

To estimate the generalization error of the classifiers models, that use the learned optimal feature set, we employed the leave-one-out cross validation (LOOCV) technique on the set of segmented ROIs. In each leave-out trial one sample is held out and used for testing. The remaining samples are used for training, and the optimal parameters are learned using this set. The output of SVM will be 0 (non-cancer, benign nevus) or 1 (cancer, MM). To combine the results of the four classifiers, we sum their outputs. A skin lesion is judged as cancer if the sum value is grater than 1.

The columns "color", "border", "asymmetry", "texture", and "combine" of Table V shows the performance of the system on SET1 for each feature category (by using selected features after feature selection step) and their fusion using the sum-rule. The results obtained by the system are balanced accuracy 85.58%, sensitivity of 84.83% and specificity of 86.32%. Visualization of the SVM output of LCF after dimension reduction and color-coding by clinical labels reveals a good separation of region corresponding to each lesion class (see FIG. 10). This suggests that distinct color characteristics are present for different skin lesion classes which are identified by the classifier. Particular image samples in FIG. 10 demonstrate how the proposed scheme allows a good separation of skin lesions.

TABLE V

The classification performance of the proposed system on the SET1. The accuracy is computed for each feature category and also for the combination of the four categories. The length of each feature categories is also provided. The values in bold correspond to the best performance.

| | | \multicolumn{7}{c}{Feature category} | | | | | | |
|---|---|---|---|---|---|---|---|---|
| | | color | border | asymmetry | texture | $LBP_S$ | combine | $combine_{LBP}$ |
| Length | | 3 | 2 | 1 | 3 | 36 | 9 | 42 |
| SET1 | Sens | 82.08 | 50.74 | 32.83 | 64.17 | 82.08 | 84.83 | 88.06 |
| | Spec | 89.74 | 82.90 | 93.16 | 79.48 | 87.17 | 86.32 | 92.30 |
| | Acc | 85.91 | 66.82 | 62.99 | 71.83 | 84.63 | 85.58 | 90.18 |

In order to evaluate the outcome of the LBPS for the overall system, we split the texture category in two subcategories:

The one defined by the optimal texture features obtained using our feature selection criterion (see Table III), which consists of GLMC-based features and edge density.

The one comprising the sign of the LBP, which did not undergone any feature selection process.

The comparison between the LBPS and the selected texture features, in terms of classification accuracy and feature length, is also given in the columns "texture" and "LBPS" of Table V.

As we can observe, rotation-invariant LBPS features provide better classification accuracy than the texture feature set based on GLCM and edge density, for the analyzed dataset. Furthermore, the estimated classification accuracy when combining the rotation invariant LBPS with the color, border and asymmetry feature categories for the system is 90.18% (column "combineLBP" of Table V). To better understand the performance of the system, when considering the texture features, we show the confusion matrices for the best two approaches in Table VI.

TABLE VI

Confusion matrices showing the true label (rows) vs. assigned label (column) for two best approaches.

| | combine | | $combine_{LBP}$ | |
|---|---|---|---|---|
| | Benign | MM | Benign | MM |
| Benign | 101 | 16 | 108 | 9 |
| MM | 10 | 56 | 8 | 59 |

Thus, LBP features can be considered a viable solution for the skin cancer image classification task. However, the difference between LBPS and GLCM derived features is in their length which constitutes a important overhead for the overall system that needs to be deployed on mobile platform.

E. Mobile Implementation and Design

We implement our proposed image analysis engine on a consumer electronic mobile device, i.e., Samsung Galaxy S4 Zoom, with Dual-core CPU running at 1.5 GHz Cortex-A9, GPU: Mali-400, RAM: 1.5 GB and storage memory of 8 GB. The features of the backside camera (the one used during the tests) are: 16 MP, image size: 4608 3456 pixels, with autofocus and 10 optical zoom.

Because the image taken by the mobile phone could have a big size, the image is resized to 512 pixels on its longest edge, using cubic interpolation with anti-aliasing enabled, before feeding it into the detection pipeline, in order to reduce the processing time and the memory footprint. The average processing time spent for each image is less than 5 seconds. It is worth to point out that, the mobile phone implementation of the algorithm has not been optimized (at instruction level) or explicitly parallelized using the available GPUs.

The subjects selected for this example, which aimed to understand the best designing principles for self-diagnosis applications, were recruited through a local community center (i.e., older participants with =63.0 and =4.76) and from a local university (i.e., young participants with =24.1 and =3.22). The whole evaluation study last for 1.5 hours.

In the first round of the example, a "Wizard-Of-Oz" mobile interface was created with three "false" diagnosis tasks, namely, psoriasis test, skin-cancer test and skin-allergy test. Participants were required to use a self-diagnosis mobile task. By choosing a specific test, participants were required to take a photo of the arm skin, and then to lunch the diagnosis. A progress bar was used to indicate the processing time, which was deliberately set to one minute. The participants were told that they could terminate the diagnosis at any point during the processing time by clicking the "Stop" button.

To explore the impact of the negative psychological effects onto participants, we devised the results of all diagnosis as "No indication of the disease". After the session, the researcher debriefed to participants that the reliability of self-diagnosis applications need to be further verified. Thus, the results showed were manipulated for the research purpose and we suggested the participants to consult professional doctors if they were interested to understand their health condition 851 towards the presented disease.

In the second round we conducted semi-structured interviews with participants exposed to our prototype. Since self-diagnosis application is a subset of personal informatics systems, we constructed our interview questions based on the structure of stage-based model to identify the design challenges across the entire adoption process. Some important aspects regarding acceptance, collection, integration, reflection, and action, which emerge from the study are:

Acceptance. The "perceived harmfulness" (in particular relevant to the older subjects), the "perceived ease of use", the "perceived usefulness" and psychological negative effects of knowing the diagnosis result (relevant for both type of subjects).

Reflection. The subjects' concerns regarding explicit classification.

Action. The trustfulness of the diagnosis result stimulates the subjects to perform certain actions (e.g., reserve a hospital visit).

EXAMPLE 3—EFFICIENT AND ACCURATE IMAGE SEGMENTATION

Although segmentation problem is classic and has a wide range of state-of-art algorithms, the problem of image segmentation under severe memory and computation constraints simultaneously has not been well studied. In this paper, we put our interest on the segmentation problem under simultaneous memory and computation constraints. Our contribution is that given a "good" segmentation method (i.e. one with good segmentation accuracy such as MST-based or Ncut or multiscale Ncut), we propose a framework that can significantly reduce the memory usage and computation time, while achieving comparable and state-of-the-art accuracy. Our solution uses simple, standard pixel-domain downsampling, which is fast and supported in some display hardware. However, it is different from other downsampling-based approaches. Instead of building a pyramid containing the image at different scales and performing the segmentation on the pyramid, we downsample the image only once.

The motivation of our one-time downsampling-based segmentation approach comes from an intuitive observation. Given a good segmentation method, even if we run the segmentation on the downsampled version of the input image, the general shapes of segments can still be determined. However, the detail of segment boundaries could be inaccurate. If we consider a segment as a combination of general shapes and boundary details, the general shape information can be obtained from the downsampled image by using a coarse segmentation, while boundary detail information can be determined from the neighborhoods of the coarse segment boundaries. By separating segment information into two parts (general shapes and detail boundaries), we can compute them in separate steps.

Based on this observation, we first apply standard pixel-domain downsampling on an input image. Then, we perform segmentation on the downsampled image (coarse segmentation). From this coarse segmentation result, we compute uncertain regions, where pixel labels need to be further refined. Finally, we refine uncertain regions to obtain the segment boundary details. The key to achieve reduced computation and memory requirement is that the total size of the downsampled image and the uncertain regions are much smaller than the size of the original image.

There are two crucial problems needed to be addressed in order to achieve competitive accuracy using this simple framework. First, we need to carefully identify the pixels that require refinement in the neighborhoods of the coarse segment boundaries. If we miss some pixels with uncertain labels during the refinement, segmentation accuracy would be degraded. On the other hand, if we include more pixels than necessary, we would perform excessive computation in the refinement. Efficiency of the overall framework would be compromised. Therefore, we propose to examine the effect of downsampling on segmentation using a signal processing analysis, thereby pixels with uncertain labels can be located. We model the image edges and perform an analysis to determine the uncertain region. Second, we need to refine the labels of uncertain pixels in an efficient and accurate way. The label information of the pixels adjacent to the uncertain pixels should be properly leveraged. Preferably, the refinement algorithm should have linear complexity with the number of image pixels. We cast the refinement as a problem to propagate the label information into the uncertain region from the adjacent certain pixels. We propose an efficient MST-based method, specifically a Kruskal-like algorithm, to perform this label propagation. Note that while Kruskal-like algorithm has been proposed for general image segmentation, it has not been applied to a label propagation problem to the best of our knowledge. Compared to general image segmentation, there are additional requirements that need to be satisfied for label propagation, as will be discussed. We apply this proposed framework and use a standard segmentation method for the downsampled images (Ncut, MST-based algorithm, or multiscale Ncut). Extensive experiments suggest that we can achieve state-of-the-art accuracy while requiring much less computation and memory than other work.

Many segmentation methods have been proposed. These methods can be divided into two categories. The first category is boundary detection-based approaches, which partition an image by discovering closed boundary contours. The second category is region-based approaches, which group together pixels being neighbours and having similar values and split groups of pixels having dissimilar value. Our proposed method can be seen as a region-based approach. Hence, we present here a brief of the state of the arts in region-based approaches.

Methods in region-based approaches usually represent an image as a graph G=(V, E, W), with the pixels as graph nodes V, and pixels within distance r (graph radius) are connected by a graph edge in E. A weight value W(i, j) measures the similarity between pixels i and j. The higher W(i, j), the more similarity between pixels i,j is. W can be computed using the location/illumination/texture information of pixels. The graph-based methods can be further divided into two subcategories. The first subcategory uses global information for segmenting. They usually are graph cut-based methods such as Minimum cut, Normalized cut (Ncut), variants of Ncut. The second subcategory uses local information for segmenting such as Minimum Spanning Tree (MST)-based segmentation methods [13], [14], [15], [5], [16]. Graph cut-based methods: The main idea of graph cut-based methods is to partition graph G=(V, E, W) into connected components Ai such that UAi=V and Ai ∩ Aj=∅ by omitting the edges linking these components. Graph cut-based methods try to segment image by optimizing some well-defined global objective functions. Wu and Leahy [11] defined a cut between two connected components as:

$$\text{cut}(A, B) = \sum_{u \in A, v \in B} W(u, v)$$

They proposed a method called minimum cut for image segmentation in such a way that the smallest (k−1) cuts among all possible cuts are selected and the corresponding edges are deleted to form k-subgraph partitions.

It also noted that the minimum cut criteria favors the formation of small segments containing only a few isolated nodes, resulting in over-segmentation. To overcome this drawback, Shi and Malik [6] proposed a new measure of disassociation between two components. Instead of looking at the value of total edge weights connecting the two partitions, they compute the cut cost as a fraction of the total edge connections to all the nodes in the graph. This new measurement called normalized cut is defined as:

$$N cut(A, B) = \frac{\text{cut}(A, B)}{\text{assoc}(A, V)} + \frac{\text{cut}(A, B)}{\text{assoc}(B, V)}$$

where $\text{assoc}(A, V) = \sum_{u \in A, t \in V} W(u, t)$ is the total connection from nodes in A to all nodes in the graph; assoc(B, V) is similarly defined. The problem of segmenting an image to k regions is turned into problem of finding of the smallest (k−1) normalized cuts.

Graph cut-based methods usually give good segment results however they are very time-consuming. For example, for Ncut method [6], the authors showed that exact minimization of normalized cut is NP hard. Hence, they proposed an approximation algorithm relating to solving a generalized eigenvalue problem having complexity $O(n^3)$ where n is number of pixels in image. In case the graph is sparse, e.g. each node (pixel) connects to only neighbors being inside a small graph radius r (e.g. r<10), the complexity is reduced to $O(n^{3/2})$. Because of its complexity, several works based on multiscale approach are proposed to accelerate Ncut.

Multiscale Graph Cut-Based Approaches:

In earlier work, at the beginning, they created a sparse graph e.g. each pixel connects to its four nearest neighbors. To find the minimal Ncuts in the graph, they recursively coarsened the graph using a weighted aggregation procedure in which they repeatedly selected smaller sets of representative pixels. The goal of these coarsening steps is to produce smaller and smaller graphs that well represent the same minimization problem. By using this process, segments that are distinct from their environment will emerge and they are detected at their appropriate size scale. After constructing the entire pyramid and detect segments at different levels of the pyramid, they scanned the pyramid from the top down performing relaxation sweeps to associate each pixel with the appropriate segment. Earlier work showed that the running time of their algorithm is linear to number of pixel of image.

Also, earlier work showed that if one increases number of neighbors of a node (e.g. increase graph radius r), a larger r generally makes the segmentation of Ncut better. However, increasing r also increases computation time. They also showed that large radius graphs can be decomposed into different scales and each of them contains connections with specific range of spatial separation. Hence, they adapted a multiscale approach for Ncut. In particular, given an image, they first downsample image at different scales s E $\{1, \ldots, S\}$. Let $X_s$ E $\{0, 1\}^{Ns><k}$ be the partitioning matrix at scale s; $N_s$ is number of pixels at scale s; $X_s(i, k)=1$ if graph node i belongs to partition k. Let $X=[X1; \ldots ; XS]$, W is a diagonal matrix where entries on the diagonal are weight matrices Wi, (i=1, ..., S) on scale levels. The multiscale Ncut segmentation can be written in the following form $$\min_X \sum_{l=1}^{k} \frac{X_l^T W X_l}{X_l^T D X_l}$$

s.t. $X \in \{0, 1\}^{N^* \times k}, X1_k = 1_{N^*}$;

$$X_{s+1}(i) = \frac{1}{\mathcal{N}_i} \sum_{j \in \mathcal{N}_i} X_s(j), \forall s = 1, \ldots, S-1.$$

Where $$N^* = \sum_{s=1}^{S} N_s \cdot j \text{ (on scale } s) \in \mathcal{N}_i$$

is sampling neighbor of i (on scale s+1). The third constraint is to make the consistent segmentation across all scales. This constraint means that the coarse-scale segmentation (Xs+1) should be locally average of the fine-scale segmentation ($X_s$). By using small graph radius (e.g. r=1) at each scale, the authors showed that the running time of multiscale Ncut is O(N). MST-based methods: Several methods in MST-based approach model an image as a MST, and the segmentation is done by cutting the tree into several sub-trees. Earlier methods do the segmentation in inverse way. At the beginning, each vertex is considered as a segment. Then, two segments are repeatedly selected to consider for merging in a greedy way. In particular, they defined that the difference between two segments is the minimum weight connecting two segments; the internal difference of a segment S is the largest edge of MST of S. Two segments will be merged if the difference between two segments is less than or equal to the minimum of the internal difference of the two segments. The authors showed that their method can produce segments which are neither too coarse nor too fine. Because only local information is used to decide if a MST should be split or if two segments should be merged, MST-based methods are usually sensitive to noise. However an advantage of these methods is that it is faster than graph cut-based methods [2]. For example, the most recent MST-based segmentation method proposed in [5] can run with the complexity O(nlogn) where n is number of image pixels. If the weights of edges are integer values (e.g. the difference in intensity of pixels), their algorithm can run in O(n).

Segmentation Result on Downsampled Image

In this section, we analyze the effect of downsampling on segment boundaries in image, thereby identifying uncertain regions, i.e., the image regions in the original resolution image where pixel labels are uncertain after the first coarse segmentation.

To simplify the discussion and analysis, we focus on 1-D image signals. Experiment results in the later sections demonstrate that this simplified analysis is reasonable and adequate for 2-D images. We consider a 1-D continuous ramp boundary signal x(l) in section III-B. The analysis for the another type of boundary, roof boundary.

Review of Image Sampling and Downsampling

Image sampling converts a continuous image signal x(l) into a sequence of discrete spatial samples $x_d[n]=x(n\Delta)$, where $\Delta$ is the sampling interval. The Nyquist-Shannon sampling theorem states that when sampling using a sampling frequency of $f_s=1/\Delta$, perfect (aliasing-free) reconstruction is possible provided that x(l) is bandlimited at $f_{max}<f_s/2$, i.e., the highest frequency component in x(l) has frequency less than $f_s/2$.

Downsampling reduces the sampling rate of the discrete signal $x_d[n]$. As the sampling rate is reduced, by the above stated Nyquist-Shannon sampling theorem, the highest frequency of the signal needs to be reduced accordingly, to avoid aliasing. In particular, downsampling with a scaling factor $\lambda$, $\lambda \leq 1$, reduces the sampling frequency to $\lambda f_s$ (the sampling interval becomes $$\frac{1}{\lambda}\Delta).$$

The signal needs to be bandlimited at $$\frac{\Delta f_s}{2}$$

to avoid aliasing. Thus, downsampling process with a scaling factor A is usually implemented as a 2-step process: (i) first, the signal is passed into a lowpass filter (anti-aliasing filter) with cut-off frequency of $\frac{\Delta f_s}{2}$, to remove the high-frequency signal components; (ii) second, the filtered signal is decimated by keeping only samples that are $\frac{1}{\lambda}\Delta$ apart. Importantly, the lowpass filtering in the first step smears the region boundary, so it complicates the computation of pixels where labels are uncertain.

Effect of Downsampling on Ramp Boundary

We first perform the analysis in the continuous domain. Later we will extend this to the discrete case for digital image. The continuous ramp boundary can be modeled mathematically by:

$$x(l) = \int_{\tau=-\infty}^{\tau=l} G(\tau; 0, \sigma_x) d\tau, \qquad (17)$$

where $G(.)$ is a Gaussian function:

$$G(\tau; \mu, \sigma) = \frac{1}{\sigma\sqrt{2\pi}} e^{\frac{-(\tau-\mu)^2}{2\sigma^2}}$$

and the ramp boundary signal x(l) is centered at l=0. The boundary steepness depends on $\sigma_x$: a large $\sigma_x$ gives a smoothly-changing boundary. The ramp boundary x(l) is illustrated in left-top of FIG. 11.

Suppose that x(l) is sampled with a sampling frequency $f_s$ and subsequently downsampled with a scaling factor $\lambda<1$. Thus the sampling frequency of the downsampled signal is $\lambda f_s$. Following the above discussion, the signal would be low-pass filtered with a cut-off frequency of $\frac{\Delta f_s}{2}$ in the first step of downsampling. For simplicity, we assume a widely-used Gaussian filter is used for low-pass filtering. The Gaussian low-pass filter with cut-off frequency of $\frac{\Delta f_s}{2}$ has an impulse response:

$$h(l) = G\left(l; 0, \frac{c}{\lambda f_s}\right), \text{ where } c = \frac{\sqrt{2\ln 2}}{\pi}$$

The low-pass filtered signal y(l) is the output of the convolution between x(l) and h(l):

$$y(l) = x(l) \otimes h(l)$$
$$= \left(\int_{\tau=-\infty}^{\tau=l} G(\tau; 0, \sigma_x) d\tau\right) \otimes G\left(l; 0, \frac{c}{\lambda f_s}\right)$$
$$= \int_{\tau=-\infty}^{\tau=l} G(\tau; 0, \sigma_y) d\tau$$

Where $\sigma_y = \sqrt{\sigma_x^2 + \left(\frac{c}{\lambda f_s}\right)^2}$

The low-pass filtered signal y(l) is illustrated in left-bottom of FIG. 11. Note that $\sigma_y \geq \sigma_x$, the low-pass filtered boundary y(l) spreads over a larger extent compared to x(l).

Suppose a segmentation algorithm on y(l) identifies $l=b_y$ as the boundary position of adjacent segments. If the segmentation works properly, $b_y$ will reside in the interval where y(l) transits from one segment to another. While the precise value of by may be different for different segmentation algorithms, a properly working algorithm should return a value of by within the segment transition interval. In this analysis, we assume $b_y \in B_y = [-2\sigma, 2\sigma_x]$. That is, we assume a properly working segmentation returns the boundary position within ±2 y of the inflection point (at l=0). Likewise, we assume if segmentation is performed directly on the original signal x(l), $b_x$ would be determined as the boundary position, where $b_x \in B_x = [-2 \sigma_x, 2\sigma_x]$.

Given $b_y$, the segmentation result on y(l), we would like to determine a refinement interval R such that refinement processing inside R can possibly identify $b_x$ (thereby, applying segmentation on the downsampled image and subsequent refinement in R can produce the same result as preforming segmentation directly on the original resolution image). To achieve this, it is necessary that R overlaps with $B_x$, so that 324 refinement in R can possibly locate $b_x$ (refer to FIG. 11(a)). Recall $b_y \in B_y = [-2\sigma_y, 2\sigma_x]$, thus $-2\sigma_y$ or $2\sigma_x$ may be returned as $b_y$ by the coarse segmentation in the extreme cases. Thus, $$R=[b_y-(2\sigma_y-2\sigma_x)-\in, b_y+(2\sigma_y-2\sigma_x)+\in] \quad (18)$$

Where $\in$ is a small positive constant, is sufficient for overlapping between R and $B_x$. Therefore, with the choice of R given by (18), it is possible to locate $b_x$ during the refinement of R. So far our discussion has been focusing on the continuous case. In the discrete case, quantization effect needs to be taken into consideration. In particular, as $b_x$ and $b_y$ need to align with the sampling positions, quantization errors with magnitudes up to half of a sampling interval may occur (refer to FIG. 11(b)). Recall that the sampling intervals of the original resolution image and the downsampled image are $\frac{1}{f_s}$ and $\frac{1}{\lambda f_s}$ respectively. Thus, in the discrete case, $$b_y \in B_y = \left[-2\sigma_y - \frac{1}{2\lambda f_s}, 2\sigma_y + \frac{1}{2\lambda f_s}\right].$$

Therefore, using $R=[b_y-\Delta_R, b_y+\Delta_R]$, where $$\Delta_R = 2\sigma_y + \frac{1}{2\lambda f_s} - \left(2\sigma_x - \frac{1}{2f_s}\right) \quad (19)$$

it is sufficient to guarantee overlapping between R and $B_x$. Note that $\Delta_R$ is half the width of the refinement interval, which centres at $b_y$, the segmentation result on y(l). Here we further simplify $\Delta_R$:

$$\Delta_R = 2\sigma_y + \frac{1}{2\lambda f_s} - \left(2\sigma_x - \frac{1}{2f_s}\right) \quad (20)$$

$$= 2\sqrt{\sigma_x^2 + \left(\frac{c}{\lambda f_s}\right)^2} + \frac{1}{2\lambda f_s} - 2\sigma_x + \frac{1}{2f_s}$$

$$\leq 2\left(\sigma_x + \frac{c}{f_s}\right) + \frac{1}{2\lambda f_s} - 2\sigma_x + \frac{1}{2f_s}$$

$$= 2\frac{c}{\lambda f_s} + \frac{1}{2\lambda f_s} + \frac{1}{2f_s}$$

$$= \frac{1}{f_s}\left(\frac{2c}{\lambda} + \frac{1}{2\lambda} + \frac{1}{2}\right).$$

Note that here we get $$\Delta_R \leq \frac{1}{f_s}\left(\frac{2c}{\lambda} + \frac{1}{2\lambda} + \frac{1}{2}\right).$$

We choose a larger value to represent $\Delta_R$; means that it is sufficient to guarantee overlapping between R and $B_x$: In particular, in practice, we set:

$$\Delta_R \leq \frac{1}{f_s}\left(\frac{2c}{\lambda} + \frac{1}{2\lambda} + \frac{1}{2}\right). \quad (21)$$

Recall that $$\Delta = \frac{1}{f_s}$$

is the sampling interval in the original resolution image. Therefore, (21) can inform the size of the refinement interval in pixels. For instance, with $$\lambda = 0.5, \Delta_R = 2.56 \frac{1}{f_s}.$$

Thus the refinement interval can be ±3 pixels around the coarse segmentation region boundary (after mapping back to the original image sampling grid). From (21), it is clear that R increases with decreasing. With more aggressive downsampling for coarse segmentation, more pixels need to be refined subsequently. Alternatively, as $\lambda<1$ when we do downsampling, it can be shown that $$\Delta_R = \frac{1}{f_s}\left(\frac{2c}{\lambda} + \frac{1}{2\lambda} + \frac{1}{2}\right) \quad (22)$$

-continued $$= \frac{1}{\lambda f_s}\left(2c + \frac{1}{2} + \frac{\lambda}{2}\right)$$

$$\leq \frac{1}{\lambda f_s}(2c+1)$$

$$= \frac{1}{\lambda f_s}\left(2\frac{\sqrt{2\ln\sqrt{2}}}{\pi} + 1\right)$$

$$\leq \frac{2}{\lambda f_s}.$$

As $$\frac{1}{\lambda f_s}$$

is the sampling interval in the downsampled image, this suggests that, w.r.t. the downsampled image sampling grid, the refinement interval can be ±2 pixels around the coarse segmentation region boundary. Note that (21) computes the size (half width) of the refinement interval w.r.t. the original image sampling grid, while (22) computes the size w.r.t. the downsampled image sampling grid.

C. Effect of Downsampling on Roof Boundary

We analyzed the effect of downsampling on ramp boundary. Here we give the analysis for another type of boundary, roof boundary. The continuous roof boundary can be modeled mathematically by:

$$x(l)=G(l;0,\sigma_x) \quad (23)$$

Similar to ramp boundary, the G(.) is a Gaussian function:

$$G(l; \mu, \sigma) = \frac{1}{\sigma\sqrt{2\pi}} e^{\frac{-(l-\mu)^2}{2\sigma^2}}$$

the roof boundary signal x(l) is centered at l=0. The boundary steepness depends on x.

The analysis of low-pass filtered signal y(l) is similar to the above section:

$$y(l) = x(l) \otimes h(l) = G(l; 0, \sigma_x) \otimes G\left(l; 0, \frac{c}{\lambda f_s}\right) = G(l; 0, \sigma_y) \quad (24)$$

where $\sigma_y = \sqrt{\sigma_x^2 + \left(\frac{c}{\lambda f_s}\right)^2}$.

Suppose a segmentation algorithm on y(l) identifies $l=b_y$ as the boundary position of adjacent segments. Similar to the earlier discussion, in this analysis, we assume boundary position $b_y \in B_y = [-2\sigma_y, 2\sigma_y]$. Likewise, for boundary position of segmentation on original signal x(l), $b_x \in B_x = [-2\sigma_x, 2\sigma_x]$.

By following the above analysis, we can obtain the same estimation about the refinement interval by (21) and (22).

After determining uncertain regions which need to be refined, we model the uncertain regions as graphs and propose to use a MST-based method (in particular, Kruskal-like algorithm) to propagate the label information from the certain regions to the uncertain regions. The reason for using MST-based method is that it can be implemented efficiently with low memory usage and its complexity is linear with the number of image pixels.

There are several MST-based segmentation methods proposed. For example, a Kruskal-like algorithm with modification in the merging decision. These algorithms are designed for general segmentation. They are not readily applicable to our label propagation problem, where the consistency of the labels in the certain and uncertain regions needs to be taken into account. Specifically, all pixels in the uncertain region should be labeled by labels coming from the certain pixels immediately connected to uncertain area. General MST based segmentation cannot guarantee that. To use a Kruskal-like algorithm to propagate labels, we propose new techniques to construct the graph and determine multiple disjunct trees. Each tree corresponds to a segment. In the followings, we will first present steps for constructing the graph to represent the uncertain region. We then present the refinement algorithm. We also prove that the proposed graph construction and refinement algorithm can satisfy the specific requirements for label propagation. Some property of the algorithm will also be discussed.

A. Graph Creation

We create a graph having nodes that are uncertain pixels. Each node is connected to its eight nearest neighbours to make edges of the graph. Weight of an edge is the absolute difference of the luminance values of its two nodes. To make it possible to propagate the labels, we also include boundary certain pixels (certain pixels that are immediately adjacent to any uncertain pixel) in the graph (FIG. 12(a)). It is important that labels in these boundary certain pixels do not change at the end of refinement. To achieve this, we introduce some virtual nodes to the graph. Each virtual node represents a specific label (a color). We also add (−1)-weight edges between boundary certain pixels and virtual nodes. Specifically, each boundary certain pixel is connected by a (−1)-weight edge to the virtual node with the same label (FIG. 2(b)). After this step, we obtain a graph G=(V; E), where V includes uncertain nodes, boundary certain nodes and virtual nodes. This graph will be the input of the proposed label propagation algorithm in the next section.

B. Label Propagation Algorithm

After creating the graph, we propose a MST-based method for relabeling uncertain pixels (white nodes in FIG. 12(b)). Our proposed method is a Kruskal-like algorithm and produce multiple disjunct trees for G. After a series of merging operations, pixels are aggregated into several segments, and labels are gradually expanded from virtual nodes to the entire graph. The final segmentation produced by our algorithm is illustrated in FIG. 12(c).

---

Algorithm 1 Label propagation algorithm

Input:
    Graph G = (V, E). V = $V_0 \cup V_1$. Where $V_0$: uncertain and boundary certain nodes (pixels); $V_1$: virtual nodes; E = $\{e_i\}_{i=1}^m$ set of edges.
Output:
    Label, label of every uncertain pixels in $V_0$;
1:  Sort E into $\{e_1, ..., e_m\}$ by non-decreasing weight order
2:  for each node v ∈ V do    ▷ Initialization
3:     MakeSet(v)
4:  end for
5:  for i = 1 → m do
6:     access node u, v from $e_i$
7:     if Find(u) ≠ Find(v) then▷ if u and v belong to two different sets
8:         if Find(u) ∉ $V_1$||Find(v) ∉ $V_1$ then   ▷ if either the set containing u or the set containing v does not have a virtual node yet
9:             Union(u, v)    ▷ merge two sets containing u and v
10:        end if
11:     end if
12:  end for

---

Algorithm 1 Label propagation algorithm

13:  for each node v ∈ $V_0$ do
14:     Label(v) ← label of (Find(v))   ▷ label of each node will be label of its root node
15:  end for
16:  return Label

---

The detail of proposed algorithm is presented in Algorithm 1 by using disjoint-set data structure with several functions: MakeSet (for creating a new set (tree) with only one node); Find (for finding the root of the tree which a node belongs to. If a tree contains a virtual node, the root of the tree will be the virtual node); Union (for merging two sets). We made a small change in Union. When merging two sets, if one set has root node which is a virtual node v, the root of both two sets will be this virtual node v. That change makes the algorithm more concise.

At the beginning, the algorithm sorts all edges in the graph by non-decreasing weight order (line 1st in Algorithm 1). The algorithm firstly considers each node of graph as an individual tree (line 2nd to 4th). Then, each edge on the graph will be examined, in the order of non-decreasing weight, to check if two different trees connected by this edge should be merged. Two different trees will be merged if at least one of them does not contain a virtual node (line 8th 463). The algorithm will result in several disjunct trees. Each tree shall contain exactly one virtual node. All nodes in each tree will be labeled by the label of virtual node belonging to that tree (line 13th to 15th). Thus, the algorithm is similar to Kruskal algorithm. The major difference is that two different sets will not be merged if both of them contain virtual nodes (line 8th). Effectively, we would not merge two sets having different labels.

C. Proof of Satisfaction of the Constraints for Refinement

In this section, we will prove that the proposed algorithm satisfies two constraints necessary for good refinement (label propagation): (i) labels of boundary certain pixels should not be changed after the refinement; (ii) all pixels in the uncertain region should be labeled by labels of boundary certain pixels.

Proof of satisfaction of constraint (i): Because the weight of edges connecting boundary certain pixels and virtual nodes equal to −1, the certain pixels will be merged with the virtual node (of the same label) first. Hence, at the end of the algorithm, the certain pixels remain with the same labels. So constraint (i) is satisfied.

Proof of satisfaction of constraint (ii): We prove satisfaction of constraint (ii) by contradiction.

Suppose in the final refinement result produced by the proposed algorithm, there is a set C not labeled. In other words, C is not connected with any virtual node. Let E(C)={e|e=<u, v>, u∈C, v∉C} be the surrounding edges of C. Because C is not connected with any virtual node, it means during the merging process, any e=<u, v>∈E(C) is not used to merge two sets containing two vertexes of e. Hence, by the merging conditions (lines 7th and 8th of Algorithm 1), either u and v belong to the same set, or u and v are connected to virtual nodes. In the first situation, C should contain v, so v∈C; in the second situation, u∈C is already connected to some virtual node, so C is labeled by this virtual node. By contradiction, constraint (ii) is satisfied.

A good property of our algorithm is that it will produce segments merged with small weight edges. Specifically:

Property 1: Let tree T be the MST of graph G'=(V$_0$; E\{(−1) weight edges}). That is, G' is the graph formed with only uncertain pixels and boundary certain pixels, with each node connecting to its eight nearest neighbors. In addition to the (−1)-weight edges, Algorithm 1 uses only edges in T for merging.

Proof of property 1: Our algorithm will first process all edges having (−1)-weight connecting V$_1$ and certain nodes.

Let us consider the edge e=<u, v> connecting two sets, u∈U, v∈V V (accessed by line 6th of Algorithm 1) and e is not a (−1)-weight edge. Then there are two cases for e regarding T: e∈T or e∉T.

If e∈T, then whether or not e is used to merge U and V, it does not affect the property 1.

If e∉T, we will prove that e will not be used to merge U and V by our algorithm.

There are two cases which can happen to U and V: U and V are the same set, or U and V are two different sets.

If U and V are the same set, then e will be not used to merge U and V (by condition in line 7th of Algorithm 1).

If U and V are two different sets, then because e∉, by property of T, there exists a path p={u∈U, . . . , v∈V}∈T which connects set U and V and w(e$_p$)<w(e), ∀e$_p$∈p, where e$_p$ is edge belonging p, and weight of an edge. So, all edges e$_p$ belonging to p were accessed by our algorithm before processing the current edge e. This implies that all nodes in p already belong to sets that have virtual nodes. That is, for node t which is the endpoint of some e$_p$, Find(t)∈V$_1$. This is because If none of the nodes in p belongs to sets with virtual nodes, then all nodes in p belong to the same set. This can be seen in lines 6th to 11th 533 of Algorithm 1 when ep was processed. This contradicts with the condition that U and V are two different sets.

If there exists at least one node in p that belongs to a set with a virtual node, then all nodes in p have already merged with other nodes that belong to sets with virtual nodes. This is due to lines 8th to 9th of Algorithm 1. Therefore, when e is processed, all nodes in p belong to sets with virtual nodes.

Therefore, both U and V already have virtual nodes, they will not be merged by e (by condition in line 8th 543 of 544 Algorithm 1).

Because small weight edges are merged with higher priority (Algorithm 1 processes edges in non-decreasing order), segments produced by Algorithm 1 will be results of merging some small weight edges of T. This ensures the quality of the refinement results.

Experimental Results

Here, we evaluate our approach on two standard well-known datasets. The first one is a single-object dataset, i.e., ground truth images have only foreground and background. This dataset contains 100 images along with ground truth segmentations. The second one is BSDS500 dataset with region benchmarks. BSDS500 contains 200 testing images. The ground truth for each image contains several boundary maps drawn by different people, forming a soft boundary map as ground truth image. We follow the earlier discussion to determine the uncertain regions. In particular, (21) and (22) are used to locate uncertain pixels around the coarse segmentation region boundaries. A pixel is marked as a segment boundary pixel if its label is different from any its 8-connected neighbors' labels. To demonstrate the performance of our approach with different segmentation algorithms, we first use MST-based algorithm, Ncut algorithm, and multiscale Ncut algorithm for the segmentation on the downsampled images in our framework. We then apply refinement on uncertain regions of the coarse segmentation results. Our framework is compared with applying MST-based algorithm, Ncut algorithm, and multiscale Ncut algorithm directly to the original resolution images. Comparisons are made in terms of segmentation accuracy, computation time and memory usage. The experiments are performed on a computer with an Intel i5-3337U 1.8 GHz CPU with 8 GB RAM. We use Matlab to downsample and upsample images. The segmentation algorithms (MST, Ncut and multiscale Ncut) for downsampled images, and our method for refinement are implemented in C, and run in Matlab using mex file. Time is measured using Matlab command. Memory usage is measured using Valgrind, a widely used profiling tool that can report memory usage.

A. Results on Single Object Dataset

1) Accuracy, time, memory performance on single object dataset: With this dataset, we measure the accuracy using Fscore. The results are computed on the average of whole dataset. In its implementation, MST-based algorithm has three parameters. It is not easy to find the optimal parameters for every different scale factor. In the experiment on single object dataset, we find the best parameters for the original resolution and the smallest scale (1/15). Then, linear interpolation is used to determine parameters for other scale factors. Ncut and multiscale Ncut algorithm has only one parameter to adjust: the number of partitions in image. For the Ncut algorithm, to make a fair comparison, we use 5 partitions which give the best performance in original image. This parameter is also used for downsampled image. For multiscale Ncut, we also find that κ partitions give the best performance in original image. We keep this parameter for downsampled image.

FIG. 13(*a-c*) show the accuracy, computation time, and memory usage when MST is used to segment downsampled image. Sometimes, the downsampled segmentation error is smaller than that error in the original image. The reason is that when images are down-sampled, the noise may be reduced. Thus, segmentation can provide more accurate shape information. When $\lambda^2 \in [0.0623, 0.3]$ it means that the scale factor $\lambda \in [0.25, 0.55]$, our method is comparable with MST in the accuracy while requiring much less time and memory. Results show that, even for a very efficient algorithm like MST, time and memory can be still saved by using our proposed approach.

The results (accuracy, time and memory) of our method and Ncut are shown in FIG. 13(*d-f*). Our method can achieve the accuracy of Ncut on original image with very limited processing time and memory. At some certain points, for example, when $\lambda^2=0:16$, our method improves the accuracy by about 2% while requiring only 2.5 s and 85 Mb compared to 25.6 s and 600 Mb of Ncut.

The results (accuracy, time and memory) of our method and multiscale Ncut are shown in FIG. 13(*g-i*). Compare to Ncut, multiscale Ncut has much lower time and memory usage. However, our method can further decrease these time and memory consuming. At certain points, for example, when $\lambda^2=0:04$, our method improves the accuracy by about 2% while requiring only 0.16 s and 5 Mb compared to 5 s and 120 Mb of multiscale Ncut.

2) Segmentation results for sample images: FIG. 14 shows the results of two sample images from the database for subjective comparison. When MST is used, the boundaries produced by MST on original image and our method are smooth and almost the same. Row (c) shows that our method get almost the same result as Ncut. An interesting result can be found in row (d). The using of Ncut on original image produced a not good result (it missed boundary on bottom-right part of the object) while our method can correct this error. This is consistent with results in FIG. 13(d) where our method gives a better Fscore at some scale factors. In row (e-f), we can see that boundaries around the object produced by multiscale Ncut and our method are smooth and almost the same.

B. Results on BSDS500 Dataset

The boundary benchmarks on BSDS has found wide acceptance for evaluation on contour detection tasks.

For segmentation, we use several region-based metrics introduced in BSDS500, including segmentation covering (Covering), Probabilistic Rand Index (PRI), and Variation of Information (VI). The Covering metric represents an evaluation of the pixel-wise classification task in recognition. PRI compares the compatibility of assignments between pairs of elements in the clusters. VI measures the distance between machine segmentation and ground-truth segmentation in terms of their average conditional entropy.

In addition, we use different parameter settings to get a series of segmentations for each image. We report three different criteria for Covering metric (ODS, OIS, and Best), and two different criteria for PRI and VI metric (ODS and OIS). Optimal dataset scale (ODS) means that we use the same parameter setting for all images in the dataset to get optimal segmentation result. Optimal image scale (OIS) means that we use optimal parameter setting for each image in the dataset to get optimal segmentation result. Best means that we find the image with best segmentation result in the dataset and report the result of this single image. For Covering and PRI metric, higher ODS (OIS, or Best) value indicates better segmentation result, while for VI metric, lower ODS (or OIS) value indicates better segmentation result.

For MST-based algorithm, we use 21 combinations of three parameters to get a collection of segmentations. For Ncut and multiscale Ncut, we use 39 different partition number to get a series of segmentations. Similar to settings used by the authors of BSDS500 dataset, for each metric, we report score with optimal scale for entire dataset (shown as ODS in Tables I-V below), and score with optimal scale for every image (shown as OIS in Tables I-V below).

TABLE I

Region benchmarks on the BSDS [22] with resize factor $\lambda = \frac{1}{12}$.

| $\lambda = \frac{1}{12}$ | BSDS500 | | | | | | |
|---|---|---|---|---|---|---|---|
| | Covering | | | PRI | | VI | |
| | ODS | OIS | Best | ODS | OIS | ODS | OIS |
| Human | 0.72 | 0.72 | — | 0.88 | 0.88 | 1.17 | 1.17 |
| MST | 0.52 | 0.58 | 0.69 | 0.79 | 0.83 | 2.26 | 1.96 |
| MST + our method | 0.51 | 0.58 | 0.69 | 0.78 | 0.83 | 1.97 | 1.71 |
| Ncut | 0.41 | 0.46 | 0.58 | 0.75 | 0.77 | 2.41 | 2.08 |
| Ncut + our method | 0.41 | 0.48 | 0.58 | 0.74 | 0.77 | 2.34 | 2.11 |
| multiscaleNcut | 0.43 | 0.51 | 0.65 | 0.77 | 0.79 | 2.28 | 1.93 |
| multiscaleNcut + our method | 0.41 | 0.48 | 0.60 | 0.75 | 0.78 | 2.35 | 2.14 |

For each segmentation method, the left three columns show the score of segmentation covering of ground-truth segments according to optimal dataset scale (ODS), optimal image scale (OIS), or Best covering criteria. The right four columns compare the segmentation methods against ground-truth using the Probabilistic Rand Index (PRI) and Variation of Information (VI) benchmarks, respectively.

TABLE II

Region benchmarks on the BSDS [22] with resize factor $\lambda = \frac{1}{8}$.

| $\lambda = \frac{1}{8}$ | BSDS500 | | | | | | |
|---|---|---|---|---|---|---|---|
| | Covering | | | PRI | | VI | |
| | ODS | OIS | Best | ODS | OIS | ODS | OIS |
| Human | 0.72 | 0.72 | — | 0.88 | 0.88 | 1.17 | 1.17 |
| MST | 0.52 | 0.58 | 0.69 | 0.79 | 0.83 | 2.26 | 1.96 |
| MST + our method | 0.53 | 0.59 | 0.71 | 0.78 | 0.83 | 1.95 | 1.71 |
| Ncut | 0.41 | 0.46 | 0.58 | 0.75 | 0.77 | 2.41 | 2.08 |
| Ncut + our method | 0.43 | 0.50 | 0.60 | 0.75 | 0.78 | 2.27 | 2.03 |
| multiscaleNcut | 0.43 | 0.51 | 0.65 | 0.77 | 0.79 | 2.28 | 1.93 |
| multiscaleNcut + our method | 0.43 | 0.49 | 0.60 | 0.75 | 0.78 | 2.32 | 2.08 |

TABLE III

Region benchmarks on the BSDS [22] with resize factor $\lambda = \frac{1}{6}$.

| $\lambda = \frac{1}{6}$ | BSDS500 | | | | | | |
|---|---|---|---|---|---|---|---|
| | Covering | | | PRI | | VI | |
| | ODS | OIS | Best | ODS | OIS | ODS | OIS |
| Human | 0.72 | 0.72 | — | 0.88 | 0.88 | 1.17 | 1.17 |
| MST | 0.52 | 0.58 | 0.69 | 0.79 | 0.83 | 2.26 | 1.96 |
| MST + our method | 0.53 | 0.60 | 0.72 | 0.79 | 0.83 | 1.96 | 1.70 |
| Ncut | 0.41 | 0.46 | 0.58 | 0.75 | 0.77 | 2.41 | 2.08 |
| Ncut + our method | 0.43 | 0.51 | 0.61 | 0.75 | 0.79 | 2.24 | 1.99 |
| multiscaleNcut | 0.43 | 0.51 | 0.65 | 0.77 | 0.79 | 2.28 | 1.93 |
| multiscaleNcut + our method | 0.44 | 0.50 | 0.61 | 0.76 | 0.79 | 2.29 | 2.04 |

TABLE IV

Region benchmarks on the BSDS [22] with resize factor $\lambda = \frac{1}{4}$.

| $\lambda = \frac{1}{4}$ | BSDS500 | | | | | | |
|---|---|---|---|---|---|---|---|
| | Covering | | | PRI | | VI | |
| | ODS | OIS | Best | ODS | OIS | ODS | OIS |
| Human | 0.72 | 0.72 | — | 0.88 | 0.88 | 1.17 | 1.17 |
| MST | 0.52 | 0.58 | 0.69 | 0.79 | 0.83 | 2.26 | 1.96 |
| MST + our method | 0.53 | 0.60 | 0.72 | 0.79 | 0.84 | 2.00 | 1.74 |
| Ncut | 0.41 | 0.46 | 0.58 | 0.75 | 0.77 | 2.41 | 2.08 |
| Ncut + our method | 0.44 | 0.51 | 0.62 | 0.76 | 0.79 | 2.22 | 1.93 |
| multiscaleNcut | 0.43 | 0.51 | 0.65 | 0.77 | 0.79 | 2.28 | 1.93 |
| multiscaleNcut + our method | 0.44 | 0.51 | 0.63 | 0.76 | 0.79 | 2.25 | 1.99 |

TABLE V

Region benchmarks on the BSDS [22] with resize factor $\lambda = \frac{1}{2}$.

| $\lambda = \frac{1}{2}$ | BSDS500 | | | | | | |
|---|---|---|---|---|---|---|---|
| | Covering | | | PRI | | VI | |
| | ODS | OIS | Best | ODS | OIS | ODS | OIS |
| Human | 0.72 | 0.72 | — | 0.88 | 0.88 | 1.17 | 1.17 |
| MST | 0.52 | 0.58 | 0.69 | 0.79 | 0.83 | 2.26 | 1.96 |
| MST + our method | 0.53 | 0.59 | 0.70 | 0.79 | 0.83 | 2.08 | 1.84 |
| Ncut | 0.41 | 0.46 | 0.58 | 0.75 | 0.77 | 2.41 | 2.08 |
| Ncut + our method | 0.42 | 0.50 | 0.62 | 0.75 | 0.78 | 2.27 | 1.95 |
| multiscaleNcut | 0.43 | 0.51 | 0.65 | 0.77 | 0.79 | 2.28 | 1.93 |
| multi scaleNcut + our method | 0.44 | 0.52 | 0.64 | 0.77 | 0.80 | 2.24 | 1.93 |

1) Accuracy, Time, Memory Performance on BSDS500 Dataset:

FIG. 15(*a-c*) show the Covering according to optimal dataset scale (ODS), computation time, and memory performance using MST to segment downsampled image. Similar to the results in FIG. 13 for single object dataset, when $\lambda^2 \in [0.015, 0.3]$ (means that the scale factor $\lambda \in [0.125, 0.55]$), our method get comparable accuracy to MST with much less time and memory usage.

The results of Covering (ODS), time and memory of our method and Ncut are shown in FIG. 15(*d-f*). At certain point, when $\lambda^2=0.0625$, our method improves the Covering score by about 2% requiring only 1.1 s and 45 Mb compared to 37.1 s and 780 Mb of Ncut.

The results (Covering (ODS), time and memory) of our method and multiscale Ncut are shown in FIG. 15(*g-i*). At certain point, when $\lambda^2=0.16$, our method improves the Covering score by about 1% requiring only 1.2 s and 28 Mb compared to 10.3 s and 185 Mb of multiscale Ncut.

2) Region benchmarks of BSDS500 dataset: The Tables I-V show the region benchmarks of BSDS500 under a series of resize factors. In these tables we use three region-based metrics: Covering, PRI, and VI. These metrics represent the accuracy for region-based segmentation in different aspects. Covering metric is the best overlap ratio between segmentation results and ground-truth results. PRI is a metric to compare segmentation results with several ground truth results. VI gives the information difference between segmentation results and the ground-truth. We measure our method in these metrics to give comprehensive results for region-based segmentation.

From these tables we can see that for the Covering metric, when the resize factor $$\lambda = \frac{1}{12}$$

is small, our method gets lower scores compared to the three algorithms (MST, Ncut, and multiscale Ncut). As we choose the resize factors that are large enough $$\left(\lambda \geq \frac{1}{18}\right),$$

our method can get comparable results with the three algorithms. For PRI and VI metrics, when the resize factors are small $$\left(\lambda \leq \frac{1}{18}\right),$$

our method gets lower scores compared to the three algorithms (MST, Ncut, and multiscale Ncut). As we choose the resize factors that are large enough $$\left(\lambda \geq \frac{1}{6}\right),$$

our method can get comparable results with the three algorithms.

3) Segmentation results for sample images: FIG. 16 shows the results of two sample images from the database. When MST is used, the boundaries produced by MST on original image and our method are both smooth. At some region, our method ignore detail boundaries, but the larger boundaries of main objects in the images are preserved. Row (c) shows that our method get almost the same result as Ncut. In row (d), the result of our method is slightly different from Ncut, both results are able to detect main boundaries on image. In row (e-f), we can see that boundaries around the object produced by multiscale Ncut and our method are smooth and almost the same.

C. Percentage of Uncertain Area

FIG. 17 shows the percentage of pixels on uncertain area. This percentage represents the ratio of pixels that need to be refined in our method. From FIG. 17(*a*) and FIG. 17(*b*) (calculated from single object dataset and BSDS500, respectively), we can see that as resize factor increases, the percentage drops, indicating that fewer number of pixels in the image need to be refined. For MST algorithm, the percentage is higher than Ncut and multiscale Ncut algorithm.

From the experiments on single object database and BSDS500, we can see the advantage of applying our framework with other segmentation methods. When using our method to refine the downsampled segmentation results generated by other methods, if the resize factor is too small (for example, if $\lambda^2$ is less than 0.01), our method cannot give comparable results with original methods. However, with some reasonable resize factors ($\lambda^2$ ranges from 0.015 to 0.3), our method can reach the accuracy of original methods, while requiring much less time and memory consuming. Based on the experiment results on different algorithms (MST, Ncut, and multiscale Ncut), we find that when applying our framework on MST algorithm, we can get best accuracy on both single object database and BSDS500, with minimal consumption of time and memory.

CONCLUSIONS

In the present invention, we proposed (i) an efficient segmentation scheme by combining fast skin detection and fusion of two fast segmentation results; (ii) new features which efficiently capture the color variation and border irregularity of segmented lesion and (iii) an efficient mechanism for selecting features. Based on the features selected by the proposed criterion, an automatic melanoma diagnosis system using a mobile platform is proposed.

In summary, the present invention relates to a mobile imaging system for early diagnosis of melanoma. In particular, the invention relates to capturing images using a smartphone and having a detection system that runs entirely on the smartphone. Smartphone-captured images taken under loosely-controlled conditions introduce new challenges for melanoma detection, while processing performed on the smartphone is subject to strict computation and memory constraints. To address these challenges, we propose to localize the skin lesion by combining fast skin detection and fusion of two fast segmentation results. We propose new features to capture color variation and border irregularity which are useful for smartphone-captured images. We also propose a new feature selection scheme to select a small set of good features used in the final system. Our evaluation confirms the effectiveness of proposed algorithms and features. In addition, the invention includes a system that computes selected visual features from a user-captured skin lesion image, and analyzes them to estimate the likelihood of malignancy, all on an off-the-shelf smartphone.

Features used in current system are hand-design features. By using automatic feature extraction methods e.g. sparse coding, it may help to find more efficient features.

The main characteristics of the proposed approach are: an efficient segmentation scheme by combining fast skin detection and a multiscale lightweight segmentation, a new set of features which efficiently capture the color variation and border irregularity of the segmented lesions and a hybrid criterion for selecting the most discriminative features. The experimental results proves the efficiency of the prototype in accurate segmenting and classification of the skin lesion in camera phone images. We foresee several possible usage scenarios for the current solution: it could be employed by the general public for preliminary self-screening or it can assist the physicians (like a personal assistant) in the diagnosis.

Whilst there has been described in the foregoing description preferred embodiments of the present invention, it will be understood by those skilled in the technology concerned that many variations or modifications in details of design or construction may be made without departing from the present invention.

REFERENCES

1. Roberto Battiti. Using mutual information for selecting features in supervised neural net learning. *IEEE Transactions on Neural Networks*, 5:537-550, 1994.
2. M. Emre Celebi, Hassan A. Kingravi, Bakhtiyar Uddin, Hitoshi Iyatomi, Y. Alp Aslandogan, William V. Stoecker, and Randy H. Moss. A methodological approach to the classification of dermoscopy images. *Comp. Med. Imag. and Graph.*, 31(6):362-373, 2007.
3. Chih-Chung Chang and Chih-Jen Lin. Libsvm: A library for support vector machines. *ACM TIST*, 2(3):27, 2011.
4. Doukas Charalampos, Stagkopoulos Paris, Kiranoudis Chris T, and Maglogiannis Ilias. Automated skin lesion assessment using mobile technologies and cloud platforms. In *Conf Proc IEEE Eng Med Biol Soc*, pages 2444-24447, 2012.
5. Taeg Sang Cho, William T Freeman, and Hensin Tsao. A reliable skin mole localization scheme. In *Computer Vision, 2007. ICCV 2007. IEEE 11th International Conference on*, pages 1-8. IEEE, 2007.
6. D. A. Clausi. An analysis of co-occurrence texture statistics as a function of grey level quantization. *Canadian Journal of Remote Sensing*, 28(1):45-62, 2002.
7. Pablo A. Estévez, Michel Tesmer, Claudio A. Perez, and Jacek M. Zurada. Normalized mutual information feature selection. *Trans. Neur. Netw.*, 20(2):189-201, February 2009.
8. Pedro F Felzenszwalb and Daniel P Huttenlocher. Efficient graph-based image segmentation. *International Journal of Computer Vision*, 59(2):167-181, 2004.
9. Keinosuke Fukunaga. *Introduction to Statistical Pattern Recognition (2nd Ed.)*. Academic Press Professional, Inc., San Diego, Calif., USA, 1990.
10. Harald Ganster, Axel Pinz, Reinhard Rohrer, Ernst Wildling, Michael Binder, and Harald Kittler. Automated melanoma recognition. *IEEE Trans. Med. Imaging*, 20(3): 233-239, 2001.
11. Rein-Lien Hsu, Mohamed Abdel-Mottaleb, and Anil K Jain. Face detection in color images. *Pattern Analysis and Machine Intelligence, IEEE Transactions on*, 24(5):696-706, 2002.
12. H. Y. Lee, W. Y. Chay, M. B. Tang, M. T. Chio, and S. H. Tan. Melanoma: Differences between asian and caucasian patients. *Ann Acad Med Singapore*, 41:17-20, 2012.
13. Huan Liu and Lei Yu. Toward integrating feature selection algorithms for classification and clustering. *IEEE Trans. Knowl. Data Eng.*, 17(4):491-502, 2005.
14. Ilias Maglogiannis and Charalampos N. Doukas. Overview of advanced computer vision systems for skin lesions characterization. *IEEE Transactions on Information Technology in Biomedicine*, 13(5):721-733, 2009.
15. American Academy of Dermatology. What to look for: The abcde of melanoma. http://www.aad.org/spot-skin-cancer/understanding-skin-cancer/how-do-i-check-my-skin/what-to-look-for/, Accessed Mar. 6, 2013.
16. Nobuyuki Otsu. A threshold selection method from gray-level histograms. *Automatica*, 11(285-296):23-27, 1975.
17. Hanchuan Peng, Fuhui Long, and Chris Ding. Feature selection based on mutual information: criteria of max-dependency, max-relevance, and min-redundancy. *IEEE Transactions on Pattern Analysis and Machine Intelligence*, 27:1226-1238, 2005.
18. Hanchuan Peng, Fuhui Long, and Chris Ding. Mrmr faq. http://penglab.janelia.org/proj/mRMR/FAQ_mrmr.htm/, Accessed Mar. 6, 2013.
19. Kiran Ramlakhan and Yi Shang. A mobile automated skin lesion classification system. In *ICTAI*, pages 138-141, 2011.
20. Elisabetta La Torre, Tatiana Tommasi, Barbara Caputo, and Giovanni Ettore Gigante. Kernel methods for melanoma recognition. In *MIE*, pages 983-988, 2006.
21. Vladimir N. Vapnik. *The Nature of Statistical Learning Theory*. Springer-Verlag New York, Inc., New York, N.Y., USA, 1995.
22. T. Wadhawan, Ning Situ, Hu Rui, K. Lancaster, Xiaojing Yuan, and G. Zouridakis. Implementation of the 7-point checklist for melanoma detection on smart handheld devices. In *Engineering in Medicine and Biology Society*, pages 3180-3183. IEEE, 2011.
23. Fei Wang, Xin Wang, Daoqiang Zhang, Changshui Zhang, and Tao Li. marginface: A novel face recognition method by average neighborhood margin maximization. *Pattern Recognition*, 42(11):2863-2875, 2009.
24. K. Weismann, H. F. Lorentzen, C. Sand, and LEO Pharma. *Der-moscopy*. LEO Pharma, 2005
25. L. Xu, M. Jackowski, A. Goshtasby, D. Roseman, S. Bines, C. Yu, A. Dhawan, and A. Huntley. Segmentation of skin cancer images. *Image Vision Comput.*, 17(1):65-74, 1999.

The invention claimed is:

1. A method for analysing analyzing an image of a lesion on the skin of a subject, the method comprising:
   (a) identifying the lesion in the image by differentiating the lesion from the skin;
   (b) segmenting the image; and
   (c) selecting a feature of the image and comparing the selected feature to a library of pre-determined parameters of the feature, wherein the feature of the lesion belongs to any one selected from the group: colour, border, asymmetry and texture of the image,
   (d) quantifying the color variation and border irregularity of the image of the lesion, wherein the irregularity of the border is determined by:
      (a) providing lines along the border;
      (b) determining the angles between two adjacent lines; and
      (c) determining the average and variance of the angles, wherein the number of lines chosen is any number 8, 12, 16, 20, 24 or 28.

2. The method according to claim 1, wherein the image is processed prior to identifying the lesion in the image.

3. The method according to claim 2, wherein processing comprises down-sampling the image.

4. The method according to claim 3, wherein segmenting the image further comprises a first segmenting and a second segmenting, the first segmenting is a coarse segmentation to determine an uncertain region on the downsampled image and the second segmenting refines the uncertain region to obtain segment boundary details.

5. The method according to claim 4, wherein the uncertain region is +/−2 pixels around the coarse segmentation region boundary.

6. The method according to claim 4, wherein the second segmenting is carried out using a MST-based algorithm.

7. The method according to claim 1, wherein the group is further divided into sub-groups and the feature is selected by comparing the feature to other features belonging to other sub-groups and other features within the same sub-group.

8. The method according to claim 1, wherein the lesion in the image is identified by comparing a colour of the skin to a library of pre-determined colours.

9. The method according to claim 1, wherein segmenting the lesion further comprising removing segments of the lesion that are connected to a skin boundary.

10. The method according to claim 1, wherein segmenting the image is a result of two segmentations,
   (a) a minimal intra-class-variance thresholding algorithm to locate smoothly-changing borders; and
   (b) a minimal-spanning-tree based algorithm to locate abruptly-changing borders.

11. The method according to claim 1, wherein segmenting is carried out by a region-based method.

12. The method according to claim 1, wherein the color variation is quantified by:
   (a) dividing image into N-partitions, each partitions further divided into M-subparts;
   (b) calculating an average pixel value for each subpart and assigning a vector to the subpart; and
   (c) determining a maximum distance between the vectors, wherein a value of N is any value 4, 8, 12 or 16; and a value of M is any value 2, 4 or 8.

13. The method according to claim 1, wherein the lesion is present in a tissue having a dermal-epidermal junction and an epidermal layer.

14. The method according to claim 1, wherein the lesion is an acral lentiginous melanoma.

15. The method according to claim 1, wherein the method further comprising acquiring the image on a computing device and the analysis is carried out on the same computing device.

16. A device for analyzing an image of an object and evaluating the risk or likelihood of a disease or condition, the system comprising:
   (a) an image capturing device for capturing the image of an object; and
   (b) a processor for executing a set of instructions stored in the device for analyzing the image, the set of instructions includes a library of algorithms stored in the device to carry out a method comprising:
   identifying the lesion in the image by differentiating the lesion from the skin;
   segmenting the image; and
   selecting a feature of the image and comparing the selected feature to a library of pre-determined parameters of the feature, wherein the feature of the lesion belongs to any one selected from the group: color, border, asymmetry and texture of the image,
   quantifying the color variation and border irregularity of the image of the lesion, wherein the irregularity of the border is determined by:
      (a) providing lines along the border;
      (b) determining the angles between two adjacent lines; and
      (c) determining the average and variance of the angles, wherein the number of lines chosen is any number 8, 12, 16, 20, 24 or 28.

17. The device according to claim 16, wherein the object is a lesion on a patient's body.

18. The device according to claim 16, wherein the disease is melanoma.

19. The device according to claim 16, wherein the device further comprising a graphical user interface for indicating to a user the results of the analysis.

20. A non-transitory computer-readable medium including executable instructions to carry out a method for analyzing an image of a lesion on the skin of a subject, the method comprising:
   (a) identifying the lesion in the image by differentiating the lesion from the skin;
   (b) segmenting the image; and
   (c) selecting a feature of the image and comparing the selected feature to a library of pre-determined parameters of the feature, wherein the feature of the lesion belongs to any one selected from the group: colour, border, asymmetry and texture of the image,
   (d) quantifying the color variation and border irregularity of the image of the lesion, wherein the irregularity of the border is determined by:
      (a) providing lines along the border;
      (b) determining the angles between two adjacent lines; and
      (c) determining the average and variance of the angles, wherein the number of lines chosen is any number 8, 12, 16, 20, 24 or 28.

* * * * *